(12) United States Patent
Murakami et al.

(10) Patent No.: US 9,952,072 B2
(45) Date of Patent: Apr. 24, 2018

(54) GAS SENSOR WITH FLOW CHANNEL FORMED BY INNER PROTECTIVE COVER

(71) Applicant: NGK INSULATORS, LTD., Nagoya-Shi (JP)

(72) Inventors: Mika Murakami, Nagoya (JP); Takayuki Sekiya, Nagoya (JP); Tomoya Seimori, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 122 days.

(21) Appl. No.: 14/948,437

(22) Filed: Nov. 23, 2015

(65) Prior Publication Data

US 2016/0076919 A1    Mar. 17, 2016

Related U.S. Application Data

(63) Continuation of application No. PCT/JP2014/064516, filed on May 30, 2014.

(30) Foreign Application Priority Data

May 31, 2013 (JP) ................................. 2013-116326

(51) Int. Cl.
 *G01N 7/00* (2006.01)
 *G01D 11/24* (2006.01)
 *G01N 27/407* (2006.01)

(52) U.S. Cl.
 CPC ....... *G01D 11/245* (2013.01); *G01N 27/4077* (2013.01)

(58) Field of Classification Search
 CPC .............. F01N 2560/02; G01N 1/2252; G01N 2291/0217; G01N 33/0037; G01N 33/225;
 (Continued)

(56) References Cited

U.S. PATENT DOCUMENTS

2004/0144645 A1   7/2004 Yamada et al.
2007/0251823 A1*  11/2007 Yamada ............. G01N 27/4077
                                                  204/424

(Continued)

FOREIGN PATENT DOCUMENTS

EP    2 388 578 A2    11/2011
JP    2007-316051 A1  12/2007

(Continued)

OTHER PUBLICATIONS

Extended European Search Report (Application No. 14803499.4) dated Dec. 13, 2016.

(Continued)

*Primary Examiner* — Walter L Lindsay, Jr.
*Assistant Examiner* — Ruth Labombard
(74) *Attorney, Agent, or Firm* — Burr & Brown, PLLC

(57) ABSTRACT

The gas sensor 100 has a gas flow channel 127 formed therein by an inner protection cover 130. The gas flow channel 127 is formed in the pathway of measured gas from a first outer gas hole 144a formed in an outer protection cover 140 that covers the tip end of a sensor element 110 to a gas inlet port 111 of the sensor element 110. The gas flow channel 127 extends from the rear end side to the tip end side of the sensor element 110 and is open to the sensor element chamber 124 having the gas inlet port 111 disposed therein.

20 Claims, 22 Drawing Sheets

(58) Field of Classification Search
CPC .. G01N 27/12; G01N 27/406; G01N 33/0009; G01N 33/0027; G01N 27/4071; G01N 27/4077; G01N 27/4076
USPC .......... 73/23.02, 23.31, 31.05; 204/426–428
See application file for complete search history.

(56) References Cited

U.S. PATENT DOCUMENTS

| | | |
|---|---|---|
| 2008/0156644 A1 | 7/2008 | Suzuki et al. |
| 2011/0126610 A1 | 6/2011 | Sekiya et al. |
| 2011/0283775 A1 | 11/2011 | Sekiya et al. |
| 2012/0255356 A1 | 10/2012 | Kume et al. |

FOREIGN PATENT DOCUMENTS

| | | |
|---|---|---|
| JP | 2008-164411 A1 | 7/2008 |
| JP | 2009-058364 A1 | 3/2009 |
| JP | 2011-112557 A1 | 6/2011 |
| JP | 2012-002803 A1 | 1/2012 |
| JP | 2012-225904 A1 | 11/2012 |
| JP | 2012-242284 A1 | 12/2012 |

OTHER PUBLICATIONS

International Search Report and Written Opinion (Application No. PCT/JP2014/064516) dated Jul. 8, 2014.
English translation of the International Preliminary Report on Patentability (Application No. PCT/JP2014/064516) dated Dec. 10, 2015.

* cited by examiner

GAS SENSOR WITH FLOW CHANNEL FORMED BY INNER PROTECTIVE COVER

BACKGROUND OF THE INVENTION

1. Field of the Invention

The present invention relates to a gas sensor.

2. Description of the Related Art

A gas sensor that detects the concentration of predetermined gas, such as NOx or oxygen, in gas to be measured such as exhaust gas of a motor vehicle has been known. Such a gas sensor may be cracked since, for example, water generated when an engine starts is deposited onto a sensor element and, thus, the temperature of the sensor element drops. To prevent such an issue, a technique to attach a protection cover to cover the sensor element is proposed. For example, PTL 1 describes a gas sensor having a double structure protection cover provided on the outer periphery of the tip end portion of the sensor element. The protection cover has a vent hole for leading exhaust gas to the inside.

CITATION LIST

Patent Literature

PTL 1: JP 2011-112557 A

SUMMARY OF INVENTION

For such a gas sensor, a demand for rapidly detecting a change in the gas concentration in measured gas, that is, a demand for increasing the responsiveness of a gas concentration detection has arisen. In addition, a demand for preventing the sensor element from being cooled by the gas flow of the measured gas has arisen in order to prevent a decrease in the detection sensitivity of the sensor element and prevent an increase in power consumption of a heater that keeps the sensor element warm. However, if, for example, the flow rate (or the flow velocity) of the measured gas flowing into the inside of the protection cover is increased in order to increase the responsiveness of gas concentration detection, the sensor element easily loses its heat. In contrast, if the flow rate (or the flow velocity) of the measured gas flowing into the inside of the protection cover is decreased in order to prevent the sensor element from cooling, it takes a long time for the measured gas to reach the sensor element and, thus, the responsiveness of detection of gas concentration decreases. As described above, in general, there is a tradeoff between the responsiveness and the heat retaining properties. Thus, there is a need for a gas sensor that can provide both quick responsiveness and excellent heat retaining properties at the same time.

To solve such a problem, it is a main object of the present invention to provide a gas sensor that provide both quick responsiveness and excellent heat retaining properties of a sensor element at the same time.

According to the present invention, a first gas sensor includes a sensor element having a gas inlet port that allows measured gas to flow thereinto and capable of detecting concentration of predetermined gas in the measured gas that has flowed into the inside through the gas inlet port, an outer protection cover having an outer gas hole formed therein, where the outer gas hole allows the measured gas to flow from the outside to the inside therethrough, and covering a tip end of the sensor element, and a gas flow channel forming member disposed between the outer protection cover and the sensor element, where the gas flow channel forming member forms a gas flow channel in the pathway of the measured gas from the outer gas hole until the gas inlet port of the sensor element. The gas flow channel extends from the rear end side to the tip end side of the sensor element and is open to a space having the gas inlet port disposed therein.

The first gas sensor according to the present invention has a gas flow channel formed therein by the gas flow channel forming member. The gas flow channel is formed in the pathway of measured gas from an outer gas hole formed in an outer protection cover that covers the tip end of a sensor element until a gas inlet port of the sensor element. The gas flow channel extends from the rear end side to the tip end side of the sensor element and is open to a space having the gas inlet port disposed therein. By providing such a gas flow channel, the measured gas that passes from the outside of the gas sensor into the space having the gas inlet port disposed therein through the outer gas hole and the gas flow channel in this order can be prevented from directly striking the surface of the sensor element (the surface other than the gas inlet port) and from passing along the surface of the sensor element for a long distance before reaching the gas inlet port. In this manner, cooling of the sensor element can be more effectively prevented. In addition, since cooling of the sensor element is prevented by forming the gas flow channel extending from the rear end side to the tip end side of the sensor element without decreasing the flow rate or the flow velocity of the measured gas, a decrease in the responsiveness of gas concentration detection can be more effectively prevented as well. Thus, the responsiveness and the heat retaining properties can be maintained at the same time.

In the first gas sensor according to the present invention, an element-side opening which is an opening of the gas flow channel adjacent to the space having the gas inlet port disposed therein may be formed at a distance A1 from the gas inlet port (a distance in the rear-end to tip-end direction of the sensor element, and a direction from the tip end toward the rear end is defined to be positive), and the distance A1 may be greater than or equal to −5 mm and less than or equal to 1.5 mm. In this manner, the element-side opening of the gas flow channel is relatively close to the gas inlet port. Accordingly, the measured gas can be prevented from directly striking the surface of the sensor element other than the gas inlet port, and the effect that prevents the measured gas from passing along the surface of the sensor element for a long distance before reaching the gas inlet port can be increased. In addition, since the element-side opening of the gas flow channel is relatively close to the gas inlet port, the responsiveness of gas concentration detection can be improved.

According to the present invention, a second gas sensor includes a sensor element having a gas inlet port that allows measured gas to flow thereinto and capable of detecting concentration of predetermined gas in the measured gas that has flowed into the inside through the gas inlet port, an outer protection cover having an outer gas hole formed therein, where the outer gas hole allows the measured gas to flow from the outside to the inside therethrough, and covering a tip end of the sensor element, and a gas flow channel forming member disposed between the outer protection cover and the sensor element, where the gas flow channel forming member forms a gas flow channel in the pathway of measured gas from the outer gas hole to the gas inlet port of the sensor element. The gas flow channel is open to a space having the gas inlet port disposed therein.

An element-side opening representing an opening of the gas flow channel adjacent to the space having the gas inlet port disposed therein is formed at a distance A1 from the gas inlet port (a distance in the rear-end to tip-end direction of the sensor element, and a direction from the tip end toward the rear end is defined to be positive), and the distance A1 is greater than or equal to −5 mm and less than or equal to 1.5 mm.

In the second gas sensor according to the present invention, the element-side opening of the gas flow channel is relatively close to the gas inlet port. Accordingly, as mentioned above in the description of the first gas sensor of the present invention, the measured gas flowing out of the element-side opening can be prevented from directly striking the surface of the sensor element other than the gas inlet port, and the effect that prevents the measured gas from passing along the surface of the sensor element for a long distance before reaching the gas inlet port can be increased. In this manner, cooling of the sensor element can be more effectively prevented. In addition, since the element-side opening of the gas flow channel is relatively close to the gas inlet port, the responsiveness of gas concentration detection can be improved. Due to these effects, the responsiveness and the heat retaining properties can be maintained at the same time.

In the first and second gas sensors according to the present invention, a plurality of the outer gas holes may be formed. A plurality of the gas flow channels may be formed. The gas flow channel forming member may be, for example, a cylindrical member. In addition, the distance A1 from the gas inlet port to the element-side opening is defined as a distance between part of the end portion of the opening of the gas inlet port that is the closest to the element-side opening and part of the end portion of the element-side opening that is the closest to the gas inlet port in the rear-end to tip-end direction of the sensor element. The element-side opening may be formed at a position so that the distance A1 from the gas inlet port is positive. That is, the element-side opening may be located away from the gas inlet port in a direction toward the rear end of the sensor element. Alternatively, the element-side opening may be formed at a position so that the distance A1 from the gas inlet port is negative. That is, the element-side opening may be located away from the gas inlet port in a direction toward the tip end of the sensor element (let the direction toward the rear end be the upward direction, and let the direction toward the tip end be the downward direction. Then, the element-side opening may be located away from the gas inlet port in the downward direction).

In the first and second gas sensors according to the present invention, the gas flow channel forming member may include a first member and a second member, and the gas flow channel may be a gap between the first member and the second member. In such a case, the first member may include a first cylinder portion that surrounds the sensor element, the second member may include a second cylinder portion having a diameter that is larger than that of the first cylinder portion, and the gas flow channel may be a cylindrical gap between the outer peripheral surface of the first cylinder portion and the inner peripheral surface of the second cylinder portion. In this manner, the gas flow channel can be formed by the first cylinder portion and the second cylinder portion of the gas flow channel forming member that have relatively simplified shapes. In this case, at least one of the outer peripheral surface of the first cylinder portion and the inner peripheral surface of the second cylinder portion may have a plurality of protruding portions formed thereon that protrude to the other surface and that is in contact with the other surface. In this manner, the positional relationship between the first cylinder portion and the second cylinder portion can be easily fixed using the protruding portions. In addition, falling off of the second member from the first member can be prevented during, for example, assembly of the gas sensor and, thus, the assembly of the gas sensor is facilitated. Note that the protruding portions may press the other surface. In this manner, the positional relationship between the first cylinder portion and the second cylinder portion can be more reliably fixed by the protruding portions.

In the first and second gas sensors each including the first member and the second member according to the present invention, the first member may include a first cylinder portion that surrounds the sensor element, and the second member may include a second cylinder portion having a diameter that is larger than that of the first cylinder portion. The outer peripheral surface of the first cylinder portion may be in contact with the inner peripheral surface of the second cylinder portion. At least one of the outer peripheral surface of the first cylinder portion and the inner peripheral surface of the second cylinder portion may have a concave portion formed thereon, and the gas flow channel may be a gap formed by the concave portion.

In the first and second gas sensors according to the present invention, the gas flow channel may be a hole that passes through the gas flow channel forming member. In this manner, the gas flow channel can be relatively easily formed.

In the first and second gas sensors according to the present invention, the gas flow channel may be formed in the pathway of the measured gas from the outer gas hole to the gas inlet port of the sensor element, and may be a flow channel that extends from the rear end side to the tip end side of the sensor element and that is parallel to the rear-end to tip-end direction of the sensor element.

In the first and second gas sensors according to the present invention, the gas flow channel may be formed in the pathway of the measured gas from the outer gas hole to the gas inlet port of the sensor element. The gas flow channel may extend from the rear end side to the tip end side of the sensor element, and the gas flow channel may be inclined so as to be closer to the sensor element toward the tip end of the sensor element from the rear end.

In the first and second gas sensors according to the present invention, the opening area of the element-side opening representing an opening of the gas flow channel adjacent to the space having the gas inlet port disposed therein may be smaller than the opening area of the outside opening representing an opening on the space side where the space has the outer gas hole disposed therein. In this manner, since the measured gas flows in through the outside opening and flows out through the element-side opening, the flow velocity of the measured gas when the measured gas flows out of the gas flow channel can be increased so as to be higher than that when the measured gas flows into the gas flow channel. Thus, the responsiveness of gas concentration detection can be improved.

In the first and second gas sensors according to the present invention, the sensor element may be disposed at a position other than an area that is on the imaginary extension of the gas flow channel from the element-side opening representing an opening of the gas flow channel adjacent to the space having the gas inlet port disposed therein. In this manner, the measured gas that flows out through the element-side opening can be prevented from directly striking the surface of the sensor element and, thus, cooling of the sensor element can be more effectively prevented.

The first and second gas sensors according to the present invention may further include a regulation member that prevents the measured gas that passes through the element-side opening representing an opening of the gas flow channel adjacent to the space having the gas inlet port disposed therein from directly flowing to the sensor element. In this manner, the measured gas that flows out through the element-side opening negligibly strikes the surface of the sensor element directly and, thus, cooling of the sensor element can be more effectively prevented. In this case, the gas flow channel forming member may include the regulation member. Alternatively, the regulation member may be a member independent from the gas flow channel forming member.

In the first and second gas sensors according to the present invention, the element-side opening of the gas flow channel representing an opening of the gas flow channel adjacent to the space having the gas inlet port disposed therein may be open in a direction from the rear end to the tip end of the sensor element and may be open parallel to the rear-end to tip-end direction of the sensor element. Note that the state in which the element-side opening is open parallel to a direction from the rear-end to tip-end direction of the sensor element implies the state in which the opening plane of the element-side opening is perpendicular to the rear-end to tip-end direction. In this manner, the measured gas can be more effectively prevented from directly striking the surface of the sensor element, and cooling of the sensor element can be more effectively prevented.

The first and second gas sensors according to the present invention may further include a bottomed cylindrical inner protection cover disposed between the outer protection cover and the sensor element, where the inner protection cover overs the tip end of the sensor element. The gas flow channel forming member may constitute at least part of the inner protection cover. In this case, the inner protection cover may have an inner gas hole formed therein, and the inner gas hole may be located away from the gas flow channel in a direction toward the tip end of the sensor element. In addition, the outer protection cover may include a cylindrical body portion having a first outer gas hole representing the outer gas hole formed therein and a bottomed cylindrical tip end portion having a second outer gas hole formed therein, where the second outer gas hole is located away from the first outer gas hole in a direction toward the tip end of the sensor element and has an internal diameter that is smaller than that of the body portion. A first gas chamber that communicates with the inside of the inner protection cover using the gas flow channel may be formed between the body portion of the outer protection cover and the inner protection cover. A second gas chamber that does not directly communicate with the first gas chamber and that communicates with the inside of the inner protection cover using the inner gas hole may be formed between the tip end portion of the outer protection cover and the inner protection cover.

DETAILED DESCRIPTION OF THE INVENTION

Figure 1A:
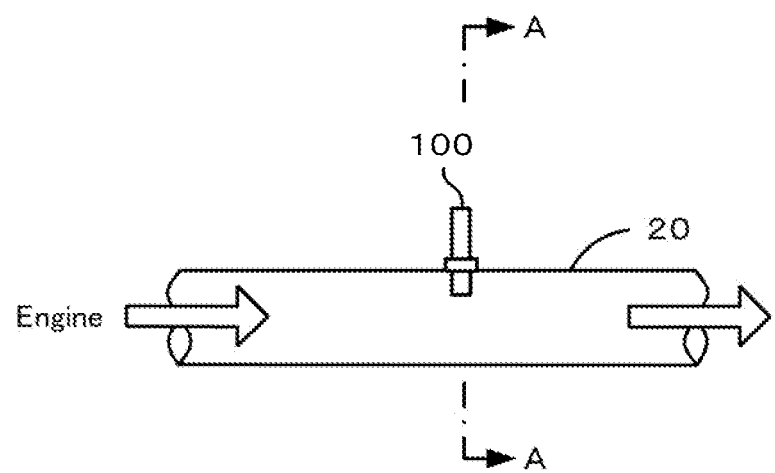
FIG. 1A and FIG. 1B are schematic illustrations of a gas sensor 100 attached to a pipe 20.
Figure 1B:
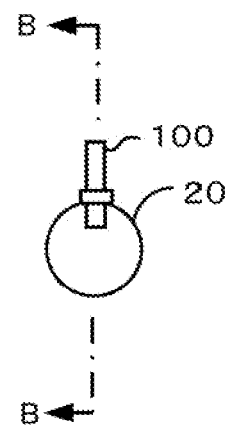
Figure 2:
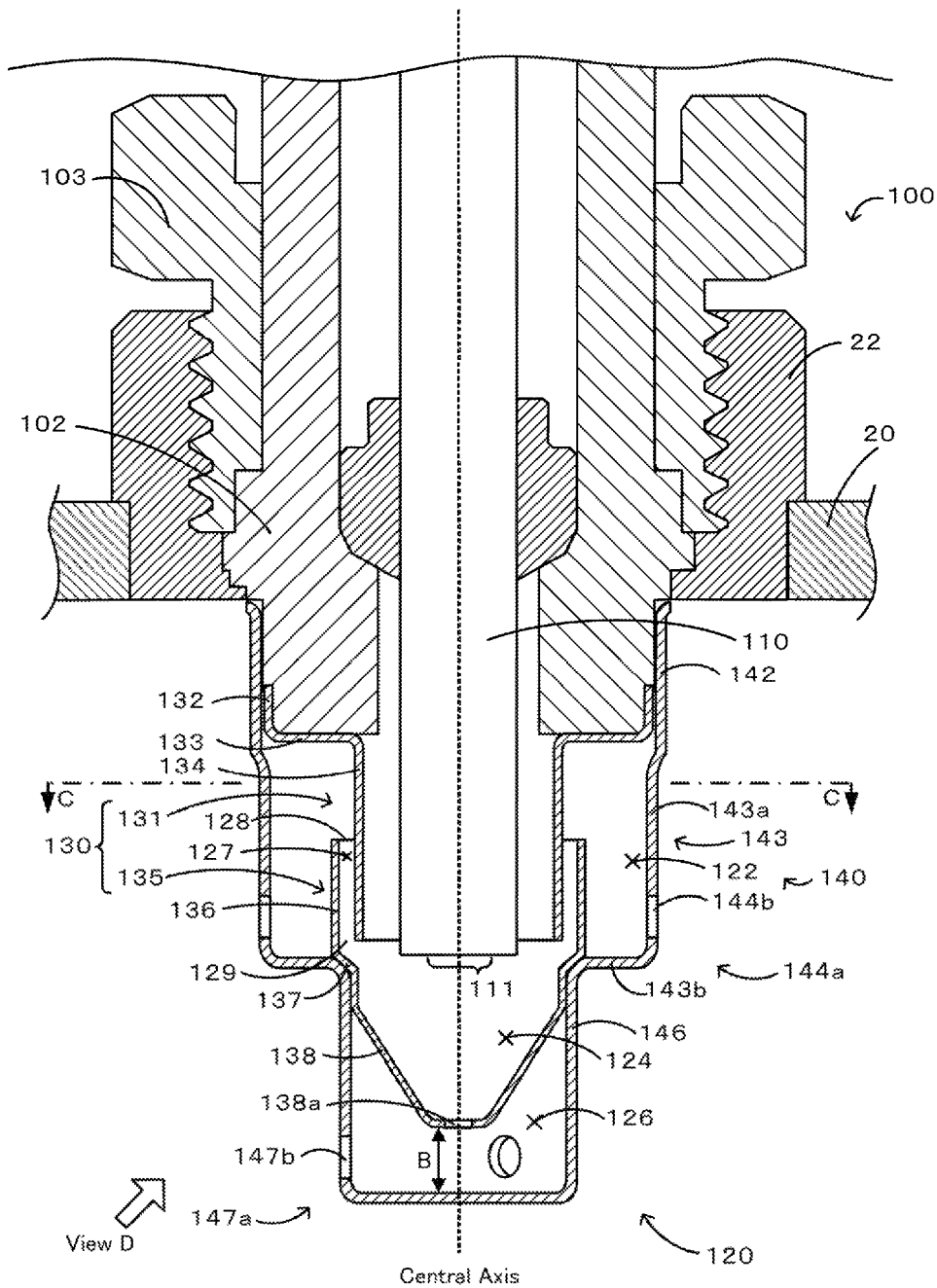
FIG. 2 is a cross-sectional view taken along a line B-B of FIG. 1B.
Figure 3:
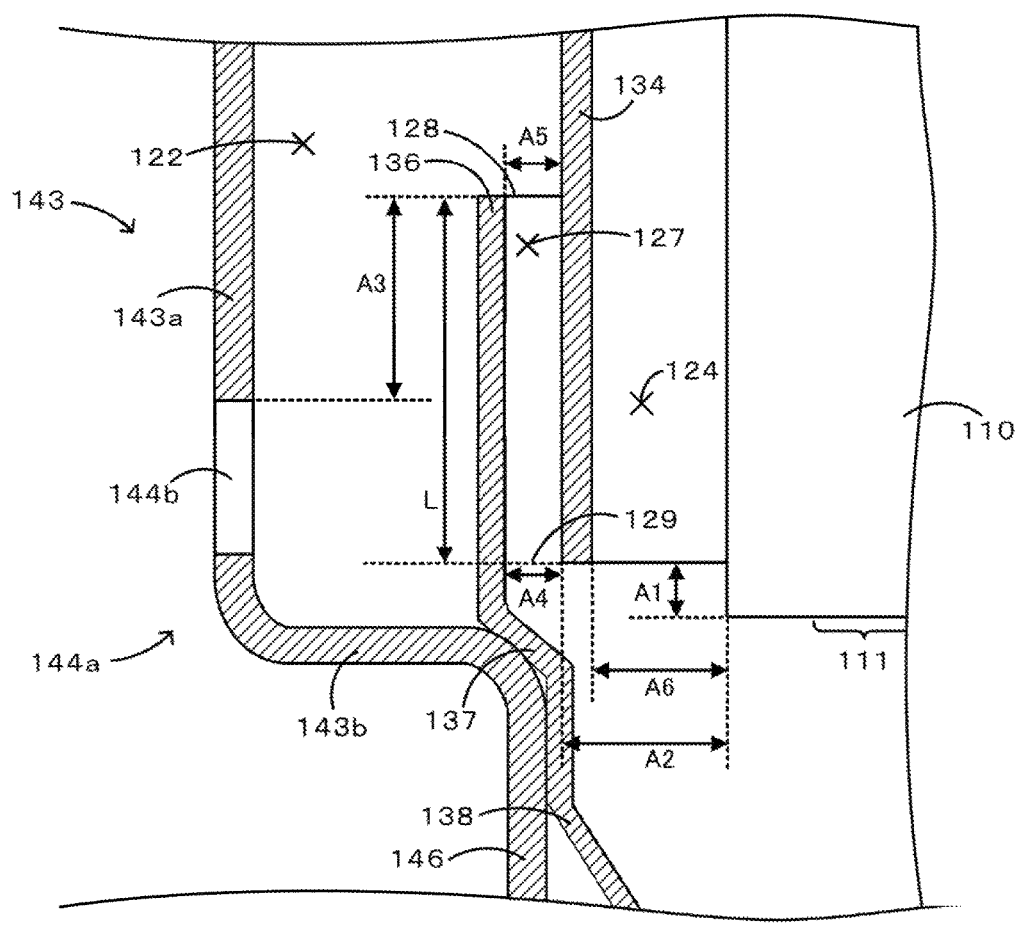
FIG. 3 is an enlarged partial cross-sectional view of a gas flow channel 127 and its vicinity of FIG. 2.
Figure 4:
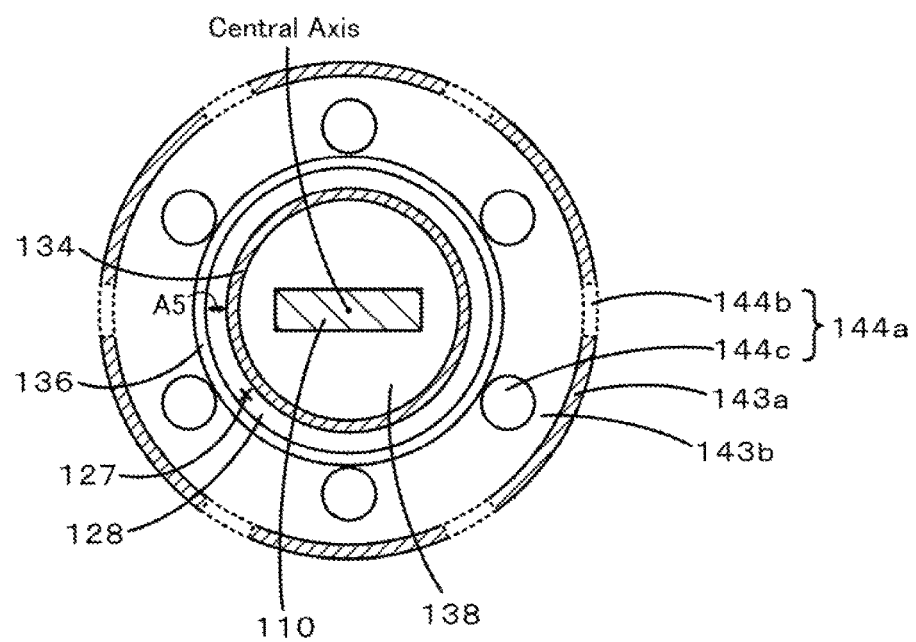
FIG. 4 is a cross-sectional view taken along a line C-C of FIG. 2.
Figure 5:
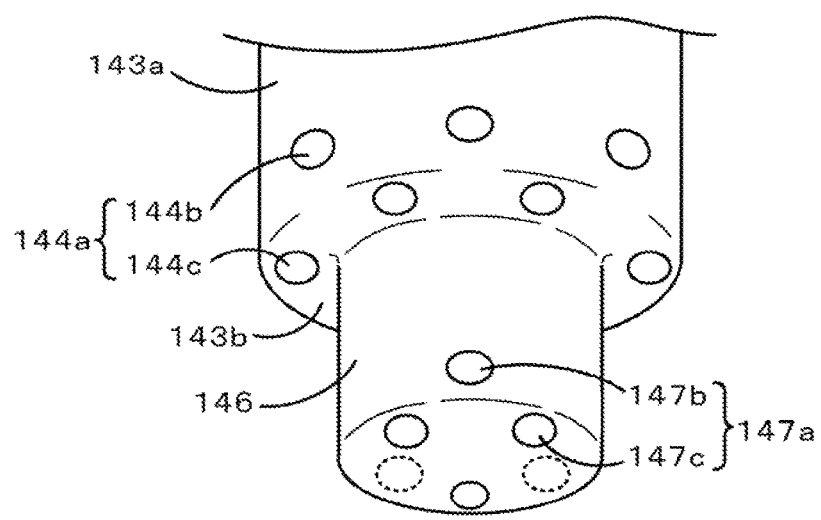
FIG. 5 is a view on Arrow D of FIG. 2.

Embodiments of the present invention are described below with reference to the accompanying drawings. FIG. 1A and FIG. 1B are schematic illustrations of a gas sensor 100 attached to a pipe 20. FIG. 1A is a view viewed from the side surface of the pipe 20, and FIG. 1B is a cross-sectional view taken along a line A-A of FIG. 1A. FIG. 2 is a cross-sectional view taken along a line B-B of FIG. 1B. FIG. 3 is an enlarged partial cross-sectional view of a gas flow channel 127 and its vicinity of FIG. 2. FIG. 4 is a cross-sectional view taken along a line C-C of FIG. 2. FIG. 5 is a view on Arrow D of FIG. 2. For convenience of description, in FIG. 2, part of the cross-sectional view taken along a line B-B of FIG. 1B is enlarged.

As illustrated in FIG. 1A, the gas sensor 100 is attached to the inside of the pipe 20, which is an exhaust channel from the engine of a vehicle. The gas sensor 100 detects the concentration of at least one of gas components, such as NOx or $O_2$, contained in exhaust gas output from an engine and serving as measured gas. As illustrated in FIG. 1B, the gas sensor 100 is fixed to the inside of the pipe 20 so that the central axis of the gas sensor 100 is perpendicular to the flow of the measured gas in the pipe 20. Note that the gas sensor 100 may be fixed to the inside of the pipe 20 so that the central axis of the gas sensor 100 is perpendicular to the flow of the measured gas in the pipe 20 and is inclined at a predetermined angle (e.g., 45°) from the vertical.

As illustrated in FIG. 2, the gas sensor 100 includes a sensor element 110 having a function of detecting the concentration of a gas component of the measured gas and a protection cover 120 that protects the sensor element 110. In addition, the gas sensor 100 includes a metal housing 102 and a metal nut 103 having a male screw formed on the outer peripheral surface thereof. The housing 102 is inserted and disposed inside a fixing member 22 welded to the pipe 20. The fixing member 22 has a female screw formed on the inner peripheral surface thereof. By further inserting the nut 103 into the fixing member 22, the housing 102 is fixed to the inside of the fixing member 22. In this manner, the gas sensor 100 is fixed to the inside of the pipe 20.

The sensor element 110 is a long and thin plate-like element. The sensor element 110 is formed from an oxygen ion conductive solid electrolyte layer, such as zirconia ($ZrO_2$). The sensor element 110 has a gas inlet port 111 that allows measured gas to enter the inside thereof and is capable of detecting the concentration of predetermined gas (e.g., NOx or $O_2$) in the measured gas that flows in through the gas inlet port 111. According to the present embodiment, the gas inlet port 111 opens on the tip end surface of the sensor element 110 (the lower surface of the sensor element 110 illustrated in FIG. 2). The sensor element 110 has a heater thereinside. The heater heats the sensor element 110 and keeps the sensor element 110 warm, that is, the heater performs temperature control of the sensor element 110. Such a structure of the sensor element 110 and a principal of detecting the concentration of a gas component are well-known and are described in, for example, Japanese Unexamined Patent Application Publication No. 2008-164411.

The protection cover 120 is disposed so as to surround the sensor element 110. The protection cover 120 includes a bottomed cylindrical inner protection cover 130 that covers the tip end of the sensor element 110 and a bottomed cylindrical outer protection cover 140 that covers the inner protection cover 130. In addition, a space surrounded by the inner protection cover 130 and the outer protection cover 140 is formed so as to serve as a first gas chamber 122 and a second gas chamber 126. Furthermore, a space surrounded by the inner protection cover 130 is formed so as to serve as a sensor element chamber 124. Note that the gas sensor 100, the sensor element 110, the inner protection cover 130, and the outer protection cover 140 have the same central axis (i.e., are coaxial).

The inner protection cover 130 is a member made of a metal (e.g., stainless steel). The inner protection cover 130 includes a first member 131 and a second member 135. The first member 131 includes a cylindrical large-diameter portion 132, a cylindrical first cylinder portion 134 having a diameter smaller than that of the large-diameter portion 132, a stepped portion 133 that connects the large-diameter portion 132 to the first cylinder portion 134. The second member 135 includes a second cylinder portion 136 having a diameter larger than that of the first cylinder portion 134, a tip end portion 138 that is located away from the second cylinder portion 136 in a direction toward the tip end of the sensor element 110 (the downward direction of FIG. 2) and that has a shape obtained by turning a circular truncated cone upside down, and a connection portion 137 that connects the second cylinder portion 136 to the tip end portion 138. In addition, the bottom surface of the tip end portion 138 has a circular inner gas hole 138a formed therein at the central point thereof. The inner gas hole 138a allows the sensor element chamber 124 to communicate with the second gas chamber 126. The diameter of the inner gas hole 138a is, for example, 0.5 mm to 2.6 mm, but is not necessarily limited thereto. Note that the large-diameter portion 132, the first cylinder portion 134, the second cylinder portion 136, and the tip end portion 138 have the same central axis. The inner peripheral surface of the large-diameter portion 132 is in contact with the housing 102. Thus, the first member 131 is fixed to the housing 102. The outer peripheral surface of the connection portion 137 of the second member 135 is in contact with and is fixed to the inner peripheral surface of the outer protection cover 140 by, for example, welding. Note that the tip end portion 138 may be formed so as to have an external diameter that is slightly larger than the internal diameter of a tip end portion 146 of the outer protection cover 140, and the tip end portion 138 may be pressed into the tip end portion 146. In this manner, the second member 135 may be fixed.

The inner protection cover 130 forms the gas flow channel 127, which is a gap formed between the first member 131 and the second member 135 (refer to FIGS. 2 to 4). That is, the inner protection cover 130 serves as a gas flow channel forming member that forms the gas flow channel 127. More specifically, the gas flow channel 127 is formed as a tubular gap between the outer peripheral surface of the first cylinder portion 134 and the inner peripheral surface of the second cylinder portion 136. The gas flow channel 127 is located in the pathway of the measured gas from a first outer gas hole 144a of the outer protection cover 140 to the gas inlet port 111 of the sensor element 110 (the gas flow channel 127 forms part of the pathway). The gas flow channel 127 includes an outside opening 128, which is an opening adjacent to the first gas chamber 122 representing a space having the first outer gas hole 144a disposed therein, and an element-side opening 129, which is an opening adjacent to the sensor element chamber 124 representing a space having the gas inlet port 111 therein. The outside opening 128 is formed away from the element-side opening 129 toward the rear end of the sensor element 110 (in the upward direction of FIG. 2). Accordingly, the gas flow channel 127 is a flow channel extending from the rear end side of the sensor element 110 (the upper side of FIG. 2) to the tip end side (the lower side of FIG. 2) of the sensor element 110 in the pathway from the first outer gas hole 144a to the gas inlet port 111. In addition, the gas flow channel 127 is a flow channel parallel to the rear-end to tip-end direction of the sensor element 110 (a flow channel extending in the vertical direction of FIG. 2).

It is desirable that the element-side opening 129 be formed at a distance A1 (refer to FIG. 3) from the gas inlet port 111 and the distance A1 be −5 mm or greater and 1.5 mm or less. Note that the distance A1 is defined as a distance in the rear-end to tip-end direction of the sensor element 110 (the vertical direction of FIG. 2), and the direction from the tip end to the rear end is defined to be positive. In addition, the distance A1 is defined as a distance between part of an end portion of the opening of the gas inlet port 111 that is the closest to the element-side opening 129 and part of an end portion of the element-side opening 129 that is the closest to the gas inlet port 111 in the rear-end to tip-end direction of the sensor element 110. For example, when, in FIG. 2, the gas inlet port is a horizontal hole that opens on the side surface of the sensor element 110 and if the element-side opening 129 is located above the upper end of the opening of the gas inlet port, a distance between the upper end of the opening of the gas inlet port and the element-side opening 129 is the distance A1, and the distance A1 is a positive value. Similarly, when, in FIG. 2, the gas inlet port is a horizontal hole that opens on the side surface of the sensor element 110 and if the element-side opening 129 is located below the lower end of the opening of the gas inlet port, a distance between the lower end of the opening of the gas inlet port and the element-side opening 129 is the distance, and the distance A1 is a negative value. Note that if, in FIG. 2, the gas inlet port is a horizontal hole that opens on the side surface of the sensor element 110 and if the element-side opening 129 is located between the upper end and the lower end of the opening of the gas inlet port, the value of the distance A1 is zero. According to the present exemplary embodiment, the element-side opening 129 is formed at the distance A1 that is positive. That is, the element-side opening 129 is formed away from the gas inlet port 111 in a direction toward the rear end of the sensor element 110 (the upward direction of FIG. 2). Note that the element-side opening 129 may be formed at the distance A1 that is negative. That is, the element-side opening 129 may be located away from the gas inlet port 111 in a direction toward the tip end of the sensor element 110 (the downward direction of FIG. 2). In addition, the element-side opening 129 is formed at a distance A2 from the sensor element 110 (refer to FIG. 3). Note that the distance A2 is a distance measured in a direction perpendicular to the tip end - rear end direction of the sensor element 110 (the right - left direction of FIG. 2). In addition, the distance A2 is a distance between part of the sensor element 110 that is the closest to the element-side opening 129 and part of the end portion of the element-side opening 129 that is the closest to the sensor element 110 in the direction perpendicular to the tip end - rear end direction of the sensor element 110. Since the distance between the sensor element 110 and the element-side opening 129 increases with increasing distance A2, the effect that prevents cooling of the sensor element 110 tends to increase with increasing distance A2. The distance A2 is, for example, in the range from 0.6 mm to 3.0 mm, but is not necessarily limited thereto. In addition, the element-side opening 129 is open in a direction from the rear end to the tip end of the sensor element 110 and is open parallel to the rear-end to tip-end direction of the sensor element 110. That is, the element-side opening 129 is open in the downward direction (the vertically downward direction) in FIG. 2. Accordingly, the sensor element 110 is disposed at a position outside an area on the imaginary extension of the gas flow channel 127 from the element-side opening 129 (an area directly beneath the element-side opening 129 of FIG. 2).

The outside opening 128 is formed at a distance A3 from the first outer gas hole 144a (refer to FIG. 3). Note that the distance A3 is a distance in the tip end to rear end direction of the sensor element 110 (the vertical direction of FIG. 2). Like the distance A1, the direction from the tip end to the rear end is defined to be positive. In addition, the distance A3 is a distance between part of an end portion of the opening of the first outer gas hole 144a that is the closest to the outside opening 128 and part of an end portion of the outside opening 128 that is the closest to the first outer gas hole 144a in the rear-end to tip-end direction of the sensor element 110. Note that according to the present embodiment, the first outer gas holes 144a are formed by horizontal holes 144b and vertical holes 144c. The upper end of the horizontal hole 144b is the closest to the element-side opening 129 in the vertical direction of FIG. 2. Accordingly, as illustrated in FIG. 3, the distance between the upper end of the horizontal hole 144b and the outside opening 128 is the distance A3. For example, when, in FIG. 2, the outside opening 128 is located below the lower end of the vertical hole 144c in the vertical direction, the distance between the lower end of the vertical hole 144c and the outside opening 128 in the vertical direction is the distance A3. Note that the outside opening 128 may be formed at a position so that the distance A3 is positive or at a position so that the distance A3 is negative. Note that it is desirable that the distance A3 be zero or greater. That is, it is desirable that the outside opening 128 be located closer to the rear end of the sensor element (on the upper side of FIG. 2) than at least one of the first outer gas holes 144a is. That is, according to the present embodiment, it is desirable that the outside opening 128 be located at the same level as the lower end of the vertical hole 144c (the lower surface of a stepped portion 143b) or at an even upper level.

The outer peripheral surface of the first cylinder portion 134 is away from the inner peripheral surface of the second cylinder portion 136 by a distance A4 in the radial direction of the cylinder in the element-side opening 129 and by a distance A5 in the radial direction of the cylinder in the outside opening 128. Each of the distance A4 and the distance A5 is, for example, 0.3 mm to 2.4 mm, but is not necessarily limited thereto. By controlling the values of the distance A4 and the distance A5, the opening area of the element-side opening 129 and the opening area of the outside opening 128 can be controlled, respectively. According to the present embodiment, the distance A4 is the same as the distance A5, and the opening area of the element-side opening 129 is the same as the opening area of the outside opening 128. Note that according to the present embodiment, the distance A4 (the distance A5) is a value that is half the difference between the external diameter of the first cylinder portion 134 and the internal diameter of the second cylinder portion 136. In addition, the distance between the element-side opening 129 and the outside opening 128 in the vertical direction, that is, a distance L of the gas flow channel 127 in the vertical direction (corresponding to the path length of the gas flow channel 127) is, for example, greater than 0 mm and less than or equal to 6.6 mm, but is not necessarily limited thereto.

Let a distance A6 be the shortest distance between the surface of the sensor element 110 and the protection cover 120 (refer to FIG. 3). Then, the effect that prevents the cooling of the sensor element 110 tends to increase with increasing distance A6. This is because as the distance A6 decreases (as the sensor element 110 and the protection cover 120 are closer to each other), the heat from the heater of the sensor element 110 is more easily removed by the protection cover 120. Note that according to the present embodiment, among parts of the protection cover 120, the inner peripheral surface of the first cylinder portion 134 of the inner protection cover 130 is the closest to the sensor element 110. Accordingly, as illustrated in FIG. 3, the distance A6 is a distance between the side surface of the sensor element 110 and the inner peripheral surface of the first cylinder portion 134 in the radial direction (the right-left direction of FIG. 3). Note that since the distance A6 is defined as the shortest distance between the sensor element 110 and the protection cover 120, the distance between the sensor element 110 and the protection cover in the axial direction (the vertical direction of FIG. 3) may be the distance A6 depending on the shape of the protection cover.

That is, the distance A6 is not limited to a distance in the right-left direction of FIG. 3. The distance A6 is, for example, 0.6 mm to 3.0 mm, but is not necessarily limited thereto. In addition, the heat from the heater tends to be more easily removed by the protection cover 120 with increasing thickness of the protection cover 120, that is, increasing heat capacity of the protection cover 120. According to the present embodiment, since the inner protection cover 130 is located close to the sensor element 110, the heat from the heater is more easily removed by the protection cover 120 with increasing thickness of the inner protection cover 130. Accordingly, the heat retaining properties of the sensor element 110 tends to increase with increasing distance A6 and decreasing thickness of the protection cover 120 (in particular, the inner protection cover 130).

The outer protection cover 140 is a member made of a metal (e.g., stainless steel). The outer protection cover 140 includes a cylindrical large-diameter portion 142, a cylindrical body portion 143 connected to the large-diameter portion 142 and having a diameter smaller than that of the large-diameter portion 142, and a bottomed cylindrical tip end portion 146 having an internal diameter smaller than that of the cylindrical body portion 143. In addition, the body portion 143 includes a side portion 143a that has a side surface extending in the direction of the central axis of the outer protection cover 140 (the vertical direction of FIG. 2) and a stepped portion 143b that is a bottom portion of the body portion 143 and that connects the side portion 143a to the tip end portion 146. Note that each of the central axes of the large-diameter portion 142, the body portion 143, the tip end portion 146 is the same as the central axis of the inner protection cover 130. The inner peripheral surface of the large-diameter portion 142 is in contact with the housing 102 and the large-diameter portion 132. Thus, the outer protection cover 140 is fixed to the housing 102. The body portion 143 is disposed so as to cover the outer peripheral surfaces of the first cylinder portion 134 and the second cylinder portion 136. The tip end portion 146 is disposed so as to cover the tip end portion 138, and the inner peripheral surface of the tip end portion 146 is in contact with the outer peripheral surface of the connection portion 137. The outer protection cover 140 has a plurality of the first outer gas holes 144a formed in the body portion 143 (12 according to the present embodiment) and a plurality of second outer gas holes 147a formed in the tip end portion 146 (six according to the present embodiment).

The first outer gas holes 144a allow the outside of the outer protection cover 140 to communicate with the first gas chamber 122. The first outer gas holes 144a include a plurality of horizontal holes 144b (six according to the present embodiment) formed in the side portion 143a at equal intervals and a plurality of vertical holes 144c (six according to the present embodiment) formed in the stepped portion 143b at equal intervals (refer to FIGS. 2, 4, and 5). Each of the first outer gas holes 144a (the horizontal holes 144b and the vertical holes 144c) is drilled so as to have a shape of a circle (an exact circle). The diameter of the 12 first outer gas holes 144a is, for example, 0.5 mm to 1.5 mm, but is not necessarily limited thereto. Note that according to the present embodiment, the diameters of the first outer gas holes 144a are all the same. However, the diameter of the horizontal holes 144b may differ from the diameter of the vertical holes 144c. Alternatively, the horizontal holes 144b may have different diameters, and the vertical holes 144c may have different diameters. In addition, according to the present embodiment, all the horizontal holes 144b are located at the same level in the vertical direction of FIG. 2, and all the vertical holes 144c are located at the same distance from the central axis of the outer protection cover 140 in FIG. 4. However, the locations are not limited thereto. Note that as illustrated in FIG. 4, the first outer gas holes 144a are formed so that the horizontal holes 144b and the vertical holes 144c are alternately located at equal intervals as viewed from the circumferential direction of the outer protection cover 140. That is, the angle formed by a line extending between the central point of one of the horizontal holes 144b illustrated in FIG. 4 and the central axis of the outer protection cover 140 and a line extending between the central point of a vertical hole 144c adjacent to the horizontal hole 144b and the central axis of the outer protection cover 140 is 30° (360°/12).

The second outer gas holes 147a are holes that allow the outside of the outer protection cover 140 to communicate with the second gas chamber 126. The second outer gas holes 147a include a plurality of horizontal holes 147b (three according to the present embodiment) formed on the side portion of the tip end portion 146 at equal intervals and a plurality of vertical holes 147c (three according to the present embodiment) formed in the bottom portion of the tip end portion 146 in the circumferential direction of the outer protection cover 140 at equal intervals (refer to FIGS. 2 and 5). Each of the second outer gas holes 147a (the horizontal holes 147b and the vertical holes 147c) is drilled so as to have a shape of a circle (an exact circle). The diameter of the six second outer gas holes 147a is, for example, 0.5 mm to 2.0 mm, but is not necessarily limited thereto. Note that according to the present embodiment, the diameters of the second outer gas holes 147a are all the same. However, the diameter of the horizontal holes 147b may differ from the diameter of the vertical holes 147c. Alternatively, the horizontal holes 147b may have different diameters, and the vertical holes 147c may have different diameters. In addition, according to the present embodiment, all the horizontal holes 147b are located at the same level in the vertical direction of FIG. 2, and all the vertical holes 147c are located at the same distance from the central axis of the outer protection cover 140. However, the locations are not limited thereto. Note that like the first outer gas holes 144a, the second outer gas holes 147a are formed so that the horizontal holes 147b and the vertical holes 147c are alternately located at equal intervals as viewed from the circumferential direction of the outer protection cover 140. That is, as viewed from the cross section perpendicular to the central axis of the outer protection cover 140, the angle formed by a line extending between the central point of one of the horizontal holes 147b and the central axis of the outer protection cover 140 and a line extending between the central point of a vertical hole 147c adjacent to the horizontal hole 147b and the central axis of the outer protection cover 140 is 60° (360°/6).

The first gas chamber 122 is a space surrounded by the stepped portion 133, the first cylinder portion 134, the second cylinder portion 136, the large-diameter portion 142, the side portion 143a, and the stepped portion 143b. The sensor element chamber 124 is a space surrounded by the inner protection cover 130. The second gas chamber 126 is a space surrounded by the tip end portion 138 and the tip end portion 146. Note that since the inner peripheral surface of the tip end portion 146 is in contact with the outer peripheral surface of the connection portion 137, the first gas chamber 122 does not directly communicate with the second gas chamber 126. In addition, the outer bottom surface of the tip end portion 138 is away from the inner bottom surface of the tip end portion 146 by a distance B. The space (the volume)

of the second gas chamber 126 tends to increase with increasing distance B. The distance B is, for example, 1.9 mm to 9.0 mm, but is not necessarily limited thereto.

The flow of the measured gas when the gas sensor 100 having such a configuration detects the concentration of predetermined gas is described below. The measured gas flowing in the pipe 20 enters the first gas chamber 122 through any of the first outer gas holes 144a (the horizontal holes 144b, the vertical holes 144c) first. Subsequently, the measured gas enters the gas flow channel 127 from the first gas chamber 122 through the outside opening 128. Subsequently, the measured gas flows out of the element-side opening 129 into the sensor element chamber 124 through the gas flow channel 127. Thereafter, when the measured gas reaches the gas inlet port 111 of the sensor element 110 inside the sensor element chamber 124, the sensor element 110 generates an electric signal (a voltage or an electric current) in accordance with the concentration of the predetermined gas (e.g., NOx or $O_2$) in the measured gas. The gas concentration is detected on the basis of the electric signal. In addition, the measured gas in the sensor element chamber 124 flows into the second gas chamber 126 through the inner gas hole 138a and flows out of the second gas chamber 126 to the outside through any of the second outer gas holes 147a. Note that the power of the internal heater is controlled by, for example, a controller (not illustrated) so that the sensor element 110 maintains a predetermined temperature.

A correspondence between a constituent element of the present embodiment and a constituent element of the present invention is described below. The gas inlet port 111 according to the present embodiment corresponds to the gas inlet port of the present invention. The sensor element 110 corresponds to the sensor element. The first outer gas holes 144a correspond to the outer gas holes. The outer protection cover 140 corresponds to the outer protection cover. The gas flow channel 127 corresponds to the gas flow channel, and the inner protection cover 130 corresponds to the gas flow channel forming member.

According to the present embodiment described in detail above, the gas sensor 100 has the gas flow channel 127 that is formed by the inner protection cover 130 in the pathway of the measured gas from the first outer gas holes 144a formed in the outer protection cover 140 that covers the tip end of the sensor element 110 until the gas inlet port 111 of the sensor element 110. The gas flow channel 127 extends from the rear end side to the tip end side of the sensor element 110 and is open to the sensor element chamber 124 having the gas inlet port 111 disposed therein. Since the gas flow channel 127 having such a structure is formed, the measured gas that flows from the outside of the gas sensor 100 into the sensor element chamber 124 through the first outer gas holes 144a and the gas flow channel 127 (in this order) flows from the rear end side to the tip end side of the sensor element 110 (the flow in the downward direction of FIG. 2). Accordingly, the measured gas that flows into the sensor element chamber 124 through the gas flow channel 127 can be prevented from directly striking the surface of the sensor element 110 (the surface other than the gas inlet port 111). In addition, the measured gas is prevented from passing along the surface of the sensor element 110 for a long distance before reaching the gas inlet port 111. That is, the measured gas does not easily strike the surface of the sensor element 110 other than the gas inlet port 111 directly. In addition, even when the measured gas strikes the surface of the sensor element 110, the distance over which the measured gas passes along the surface can be reduced. In this manner, the cooling of the sensor element 110 can be further prevented. In addition, since the cooling of the sensor element 110 is prevented by forming the gas flow channel 127 that extends from the rear end side to the tip end side of the sensor element 110 without reducing the flow rate or the flow velocity of the measured gas, a decrease in the responsiveness of gas concentration detection can be also prevented. Thus, the responsiveness and the heat retaining properties can be maintained at the same time.

In addition, if the element-side opening 129 is formed at a position so that the distance A1 from the gas inlet port 111 is −5 mm or greater and 1.5 mm or less, the element-side opening 129 is located relatively close to the gas inlet port 111. Accordingly, the effect that prevents the measured gas that flows through the gas flow channel 127 and flows into the sensor element chamber 124 from directly striking the surface of the sensor element 110 other than the gas inlet port 111 and the effect that prevents the measured gas from passing along the surface of the sensor element 110 for a long distance before reaching the gas inlet port 111 can be increased. Furthermore, since the element-side opening 129 is located relatively close to the gas inlet port, the responsiveness of gas concentration detection can be increased. Note that by setting the distance A1 to a value that is −5 mm or greater and 1.5 mm or less, these effects can be increased more.

In addition, the inner protection cover 130 includes the first member 131 and the second member 135, and the gas flow channel 127 is formed as a gap between the first member 131 and the second member 135. Furthermore, the first member 131 includes the first cylinder portion 134 that surrounds the sensor element 110, the second member 135 includes the second cylinder portion 136 having a diameter that is larger than that of the first cylinder portion 134, and the gas flow channel 127 is formed as a cylindrical gap between the outer peripheral surface of the first cylinder portion 134 and the inner peripheral surface of the second cylinder portion 136. In this manner, the gas flow channel 127 can be formed by the first cylinder portion 134 and the second cylinder portion 136 having simplified shapes.

Still furthermore, the sensor element 110 is disposed at a position outside an area that is on the imaginary extension of the gas flow channel 127 from the element-side opening 129. In this manner, the measured gas that flows out from the element-side opening 129 to the sensor element chamber 124 is more effectively prevented from directly striking the surface of the sensor element 110. Thus, the cooling of the sensor element 110 can be more effectively prevented.

Yet still furthermore, the gas flow channel 127 has the element-side opening 129 that is open in a direction from the rear end to the tip end of the sensor element 110 and that is open parallel to the rear-end to tip-end direction of the sensor element 110. In this manner, the measured gas that flows out through the element-side opening 129 to the sensor element chamber 124 is more effectively prevented from directly striking the surface of the sensor element 110. Thus, the cooling of the sensor element 110 can be more effectively prevented.

It should be noted that the present invention is not limited to the above-described embodiment in any way, and a variety of embodiments can be made without departing from the spirit and the technical scope of the invention.

Figure 6:
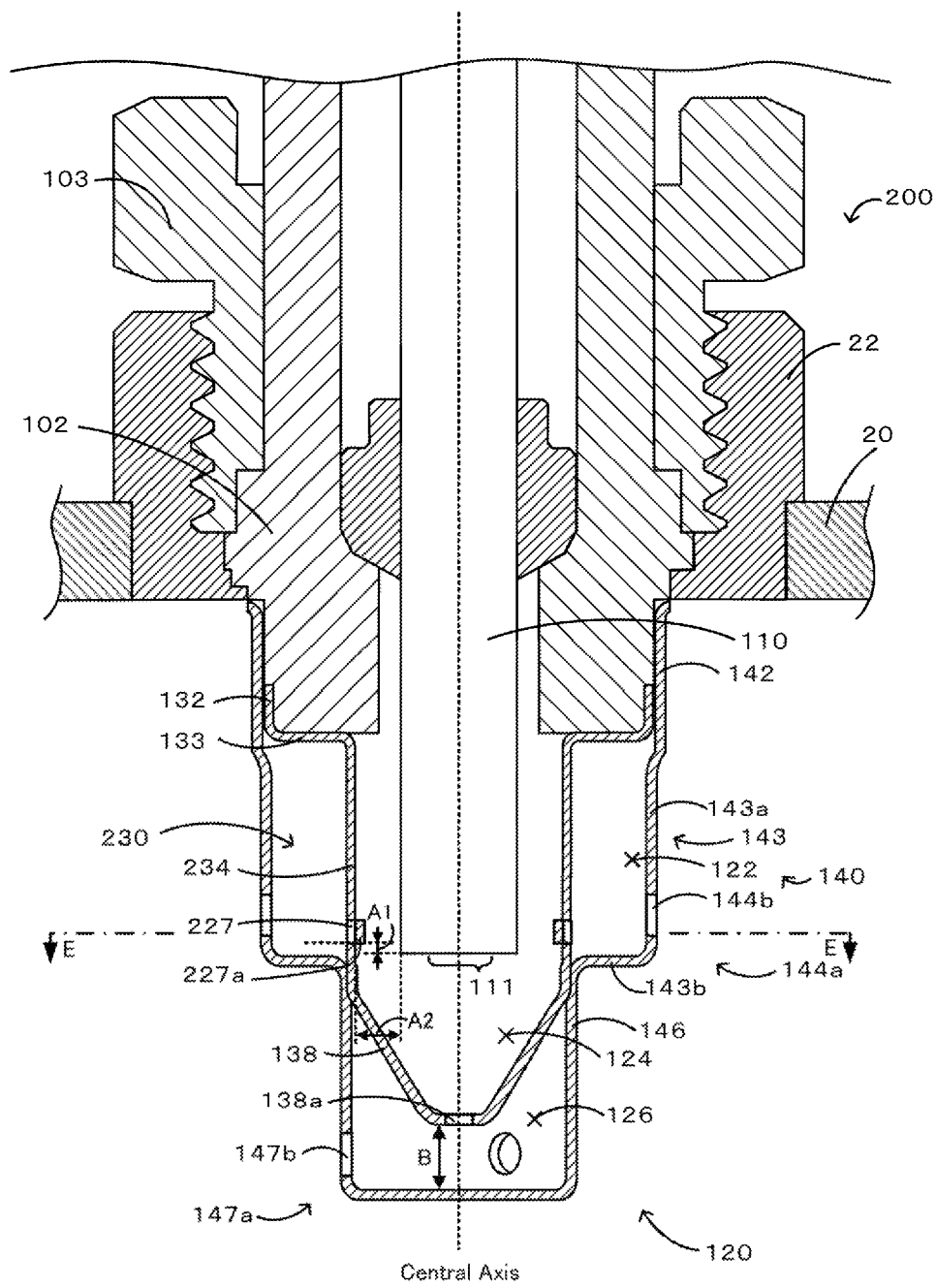
FIG. 6 is a vertical cross-sectional view of a gas sensor 200 according to a modification.
Figure 7:
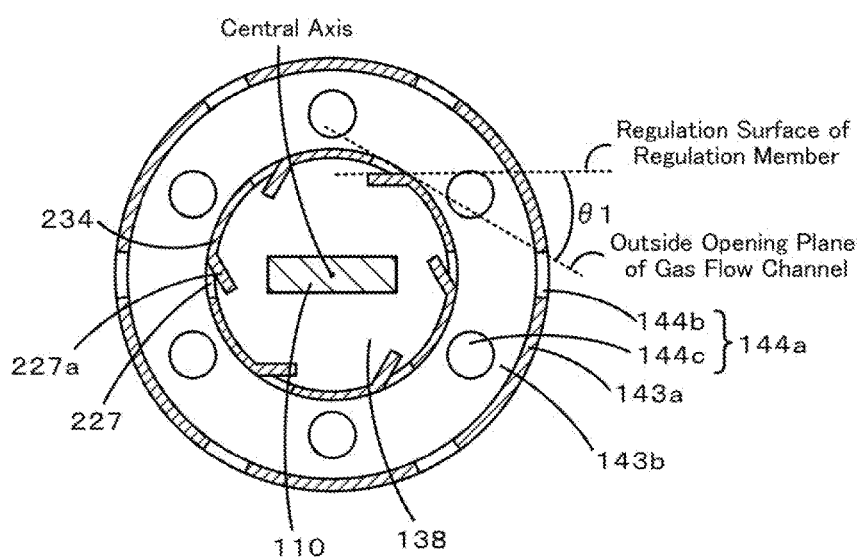
FIG. 7 is a cross-sectional view taken along a line E-E of FIG. 6.

For example, while the above embodiment has been described with reference to the gas flow channel 127 that forms a flow channel from the rear end side to the tip end side of the sensor element 110 in the pathway of the measured gas from the first outer gas hole 144a to the gas inlet port 111, the structure of the gas flow channel 127 is not limited thereto. If the distance A1 is −5 mm or greater and 1.5 mm or less, the need for forming the flow channel from the rear end side to the tip end side of the sensor element 110 may be eliminated. FIG. 6 is a vertical cross-sectional view of a gas sensor 200 according to a modification. FIG. 7 is a cross-sectional view taken along a line E-E of FIG. 6. Note that in FIGS. 6 and 7, constituent elements similar to those of the gas sensor 100 are identified with the same reference numerals, and detailed description of the constituent elements is not repeated. As illustrated in FIGS. 6 and 7, the gas sensor 200 includes an inner protection cover 230. The inner protection cover 230 is formed from a single member. Unlike the inner protection cover 130, the inner protection cover 230 does not include the first cylinder portion 134, the second cylinder portion 136, and the connection portion 137. Instead, the inner protection cover 230 includes a cylinder portion 234. The cylinder portion 234 has a diameter that is smaller than that of the large-diameter portion 132 and is connected to the large-diameter portion 132 via the stepped portion 133. In addition, the cylinder portion 234 is connected to the tip end portion 138. The central axis of the cylinder portion 234 is the same as the central axis of the tip end portion 138 and is the same as the central axis of the outer protection cover 140. The cylinder portion 234 has a plurality of through-holes formed therein (six in FIG. 6 and FIG. 7). The opening of each of the through-holes is rectangular. The inside of each of the holes serves as a gas flow channel 227. As illustrated in FIG. 7, the gas flow channels 227 are formed along the outer periphery of the cylinder portion 234 at equal intervals. The gas flow channels 227 are formed as flow channels extending in a direction perpendicular to the tip end to rear end direction of the sensor element 110 (the right-left direction of FIG. 6). In addition, the gas flow channels 227 are formed as the flow channels extending in a direction toward the central axis of the cylinder portion 234 (the radial direction) as viewed from a cross section perpendicular to the central axis. Note that the opening of the gas flow channel 227 on the inner side of the cylinder portion 234 corresponds to the element-side opening, and the opening on the outer side of the cylinder portion 234 corresponds to the outside opening. By setting the distance A1 to −5 mm or greater and 1.5 mm or less, even such a gas flow channel 227 formed as a through-hole extending in the right-left direction of FIG. 6 can be relatively close to the gas inlet port 111. Accordingly, like the above-described embodiment, the measured gas can be prevented from directly striking the surface other than the gas inlet port 111. In addition, the measured gas can be prevented from passing along the surface of the sensor element 110 for a long distance before reaching the gas inlet port 111. Furthermore, since the element-side opening is located relatively close to the gas inlet port, the responsiveness of gas concentration detection can be improved. Note that as illustrated in FIG. 6, the distance A1 of the gas sensor 200 according to the modification is defined as a distance between the gas inlet port 111 and the lower end of the element-side opening of the gas flow channel 227 in the vertical direction. Similarly, as illustrated in FIG. 6, the distance A2 is defined as a distance between the end portion of the sensor element 110 (the left end in FIG. 6) and the element-side opening of the gas flow channel 227 in the right-left direction. The distance A2 is the same as the distance between the end portion of the sensor element 110 and the inner peripheral surface of the cylinder portion 234. In addition, in the gas sensor 200 illustrated in FIG. 6, the inner peripheral surface of the cylinder portion 234 is the closest to the sensor element 110, and the distance A6 is the same as the distance A2. Note that the cylinder portion 234 has a plurality of regulation members 227a (six according to the present embodiment) formed therein at equal intervals (refer to FIG. 7). The regulation members 227a regulate the flow of the measured gas flowing into the sensor element chamber 124 through the gas flow channels 227. As illustrated in FIG. 7, the regulation members 227a are in one-to-one correspondence with the gas flow channels 227. Each of the regulation members 227a is formed between a corresponding gas flow channel 227 and the sensor element 110. In addition, the regulation members 227a are formed so as to be rotationally symmetrical (sixfold rotationally symmetrical according to the present embodiment). Furthermore, an angle θ1 (refer to FIG. 7) formed by a regulation surface of the regulation member 227a and an outside opening plane of the gas flow channel 227 is set to a value so that the measured gas that passes through the element-side opening of the gas flow channel 227 is inhibited from directly going to the sensor element 110. In this manner, the measured gas flowing out through the element-side opening negligibly strikes the surface of the sensor element 110 directly. Accordingly, cooling of the sensor element 110 can be more effectively prevented. The formed angle θ1 may be set to, for example, 20° or more and 70° or less. alternatively, the formed angle θ1 may be set to 25° or more and 67.5° or less. Note that like the gas sensor 200 according to the modification, the inner protection cover 130 serving as the gas flow channel forming member may include the regulation members 227a. Alternatively, the regulation members 227a may be members that are independent from the inner protection cover 130.

Figure 8:
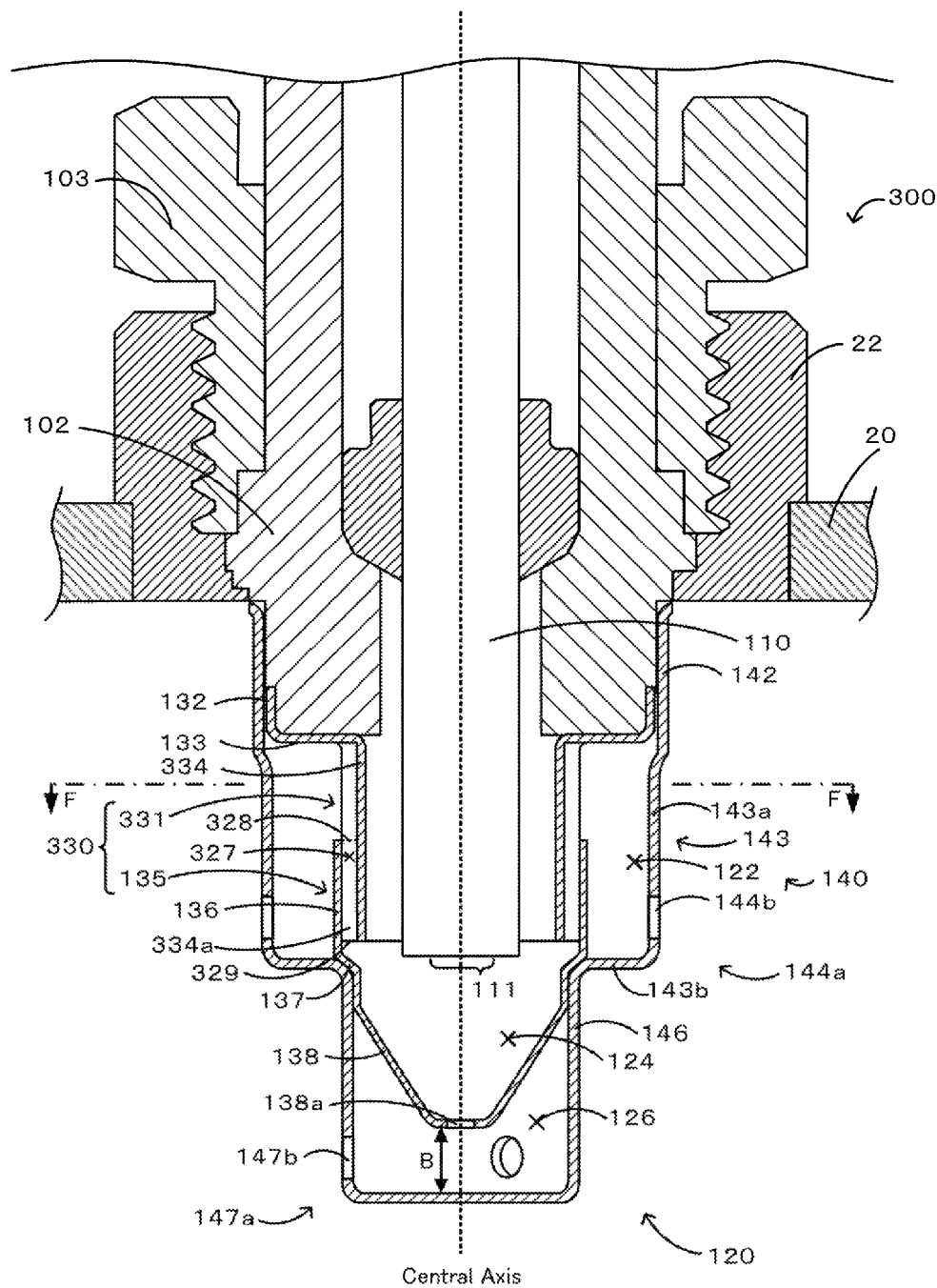
FIG. 8 is a vertical cross-sectional view of a gas sensor 300 of a modification in such a case.
Figure 9:
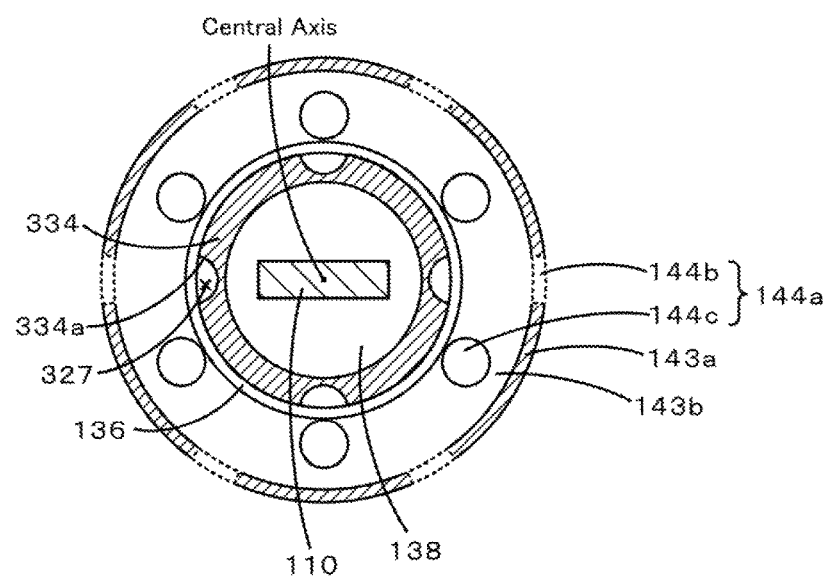
FIG. 9 is a cross-sectional view taken along a line F-F of FIG. 8.

While the above embodiment has been described with reference to the gas flow channel 127 formed as a cylindrical gap between the outer peripheral surface of the first cylinder portion 134 and the inner peripheral surface of the second cylinder portion 136, the gas flow channel 127 is not limited thereto only if the gas flow channel 127 is formed as a gap between the first member 131 and the second member 135. For example, the outer peripheral surface of the first cylinder portion may be in contact with the inner peripheral surface of the second cylinder portion, and a concave portion may be formed in at least one of the outer peripheral surface of the first cylinder portion and the inner peripheral surface of the second cylinder portion. In addition, the gas flow channel may be a gap formed from the concave portion. FIG. 8 is a vertical cross-sectional view of a gas sensor 300 of a modification in such a case. FIG. 9 is a cross-sectional view taken along a line F-F of FIG. 8. Note that in FIGS. 8 and 9, constituent elements similar to those of the gas sensor 100 are identified with the same reference numerals, and detailed description of the constituent elements is not repeated. As illustrated in FIGS. 8 and 9, the gas sensor 300 includes an inner protection cover 330. The inner protection cover 330 includes a first member 331 and a second member 135. Unlike the first member 131, the first member 331 does not include the first cylinder portion 134. Instead, the first member 331 includes a first cylinder portion 334. The first cylinder portion 334 is connected to the large-diameter portion 132 via the stepped portion 133. The first cylinder portion 334 has an external diameter that is substantially the same as the internal diameter of the second cylinder portion 136. The outer peripheral surface of the first cylinder portion 334 is in contact with the inner peripheral surface of the second cylinder portion 136. In addition, a plurality of concave portions 334a (four in FIG. 8 and FIG. 9) are formed on the outer periphery of the first cylinder portion 334 at equal intervals. As viewed from the cross section perpendicular to the tip end to rear end direction of the sensor element 110, each of the concave portions 334*a* is a groove having a shape of a semicircle or a circular arc. Each of the concave portions 334*a* is formed so as to extend from one end to the other end of the first cylinder portion 334 in the axial direction (note that the concave portion 334*a* does not pass through the top end on the stepped-portion-133 side, that is, the top end of the first cylinder portion 334 in FIG. 8). The inner protection cover 330 forms a gas flow channel 327, which is a gap between each of the concave portion 334*a* and the inner peripheral surface of the second cylinder portion 136. As can be seen from FIG. 9, a plurality of gas flow channels 327 are formed in accordance with the number of the concave portions 334*a* (six in FIG. 8 and FIG. 9). The shape of each of the gas flow channels 327 is the shape of a vertical hole. The gas flow channel 327 has the outside opening 328 which is an opening adjacent to the first gas chamber 122 and the element-side opening 329 which is an opening adjacent to the sensor element chamber 124. The gas flow channel 127 is a flow channel that is parallel to the rear-end to tip-end direction of the sensor element 110 (a flow channel extending in the vertical direction of FIG. 2). In addition, the element-side opening 329 is open in downward direction of FIG. 8 (directly beneath), and the sensor element 110 is disposed in at a position outside an area that is on the imaginary extension of the gas flow channel 327 from the element-side opening 329 (an area directly beneath the element-side opening 329 of FIG. 8). Even in the gas sensor 300, the gas flow channels 327 that extend from the rear end side to the tip end side of the sensor element 110 and that are open to the sensor element chamber 124 are formed in the pathway of the measured gas from the first outer gas holes 144*a* until the gas inlet port 111. Accordingly, like the above-described embodiment, the responsiveness and the heat retaining properties can be maintained at the same time. Note that even for the gas sensor 300, by appropriately controlling the distances A1 to A6, the distance B, and the distance L as in the above-described embodiment, the above-described effects can be obtained. In addition, while in FIGS. 8 and 9, the first member 331 has a concave portion, the concave portion may be formed in the second member 135, and a space formed by the concave portion of the second member 135 and the outer peripheral surface of the first member may be used as a gas flow channel. Alternatively, a concave portion may be formed in each of the first member 331 and the second member 135, and a space formed by the concave portion of the first member 331 and the concave portion of the second member 135 may be used as the gas flow channel. Furthermore, the shape of the concave portion is not limited to that illustrated in FIG. 9. For example, the cross section of the concave portion may be rectangular.

Figure 10:
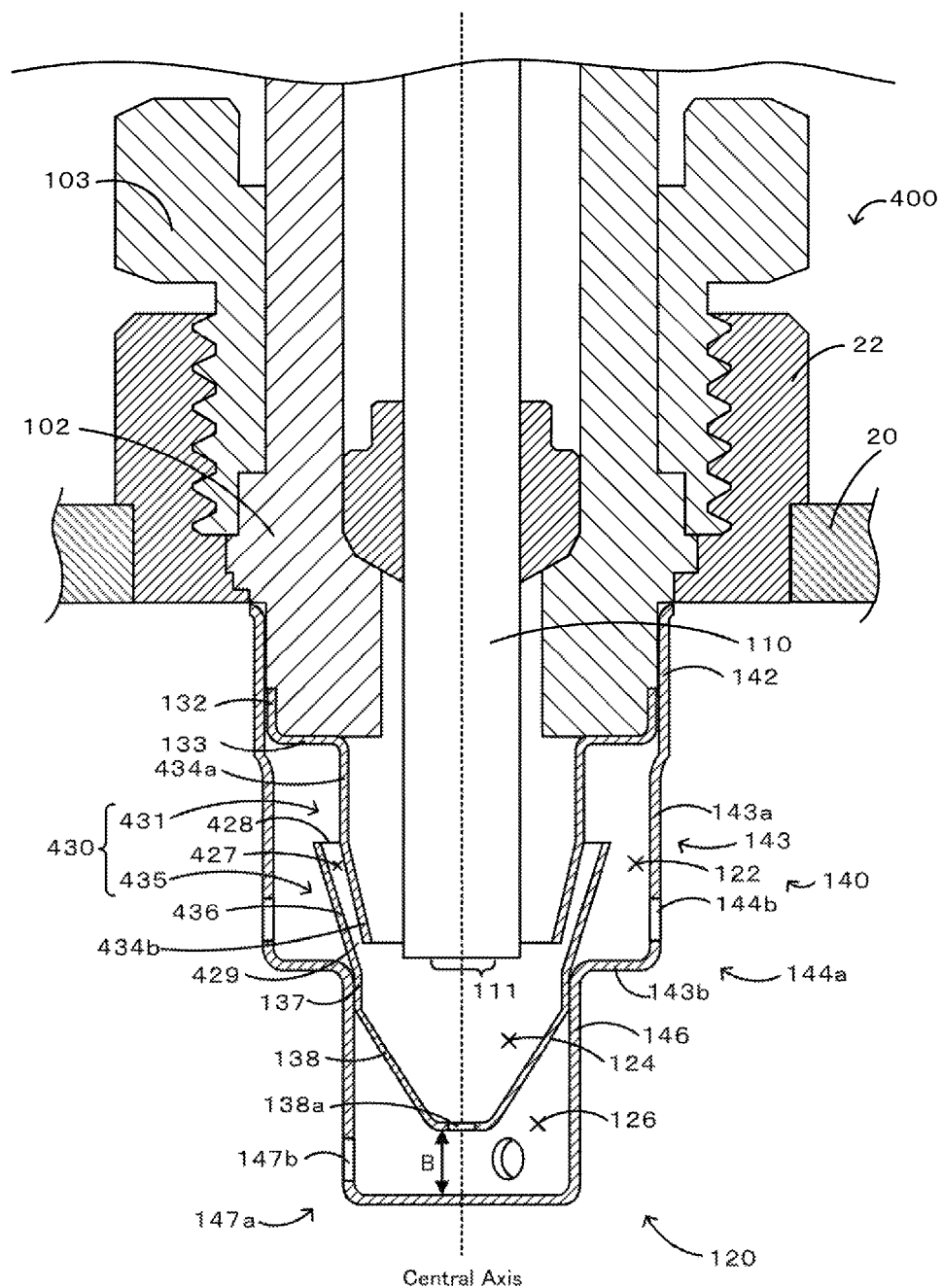
FIG. 10 is a vertical cross-sectional view of a gas sensor 400 according to a modification

While the above embodiment has been described with reference to the gas flow channel 127 that is parallel to the rear-end to tip-end direction of the sensor element 110 (the flow channel extending in the vertical direction of FIG. 2), the gas flow channel 127 is not limited thereto. For example, the gas flow channel may be a flow channel that is inclined from the rear-end to tip-end direction so as to be closer to the sensor element towards the rear end of the sensor element from the tip end. FIG. 10 is a vertical cross-sectional view of a gas sensor 400 according to a modification in such a case. Note that in FIG. 10, the constituent elements similar to those of the gas sensor 100 are identified with the same reference numerals, and detailed description of the constituent elements is not repeated. As illustrated in FIG. 10, the gas sensor 400 includes an inner protection cover 430. The inner protection cover 430 includes a first member 431 and a second member 435. Unlike the first member 131, the first member 431 does not include the first cylinder portion 134. Instead, the first member 431 includes a cylindrical body portion 434*a* and a cylindrical first cylinder portion 434*b* having a progressively reduced diameter toward the tip end of the sensor element 110 from the rear end. The body portion 434*a* is connected to the large-diameter portion 132 via the stepped portion 133. The first cylinder portion 434*b* is connected to the body portion 434*a* at the end portion adjacent to the rear end of the sensor element 110. Unlike the second member 135, the second member 435 does not include the second cylinder portion 136. Instead, the second member 435 includes a cylindrical second cylinder portion 436 having a progressively reduced diameter toward the tip end of the sensor element 110 from the rear end. The second cylinder portion 436 is connected to the tip end portion 138 via the connection portion 137. The outer peripheral surface of the first cylinder portion 434*b* is not in contact with the inner peripheral surface of the second cylinder portion 436, and the gap formed between the two serves as the gas flow channel 427. The gas flow channel 427 has an outside opening 428 which is an opening adjacent to the first gas chamber 122 and the element-side opening 429 which is an opening adjacent to the sensor element chamber 124. Due to the shapes of the first cylinder portion 434*b* and the second cylinder portion 436, the gas flow channel 427 is inclined from the rear-end to tip-end direction so as to be progressively closer to the sensor element 110 (be closer to the central axis of the inner protection cover 130) toward the tip end of the sensor element 110 from the rear end. In addition, the gas flow channel 427 is formed so that the width of the gas flow channel 427 decreases toward the tip end of the sensor element 110 from the rear end. Accordingly, the opening area of the element-side opening 429 is smaller than the opening area of the outside opening 428. That is, the distance A4 is smaller than the distance A5 of the gas flow channel 427 illustrated in FIG. 3. Even in the gas sensor 400, the gas flow channel 427 that extends from the rear end side to the tip end side of the sensor element 110 and that are open to the sensor element chamber 124 is formed in the pathway of the measured gas from the first outer gas holes 144*a* to the gas inlet port 111. Accordingly, like the above-described embodiment, the responsiveness and the heat retaining properties can be maintained at the same time. In addition, the opening area of the element-side opening 429 through which the measured gas flows out is smaller than the opening area of the outside opening 428. Accordingly, when the measured gas flows in through the outside opening 428 and flows out through the element-side opening 429, the flow rate of the measured gas that flows out is higher than the flow rate of the measured gas that flows in. Thus, the responsiveness of gas concentration detection can be improved. Note that even when the gas flow channel 427 is not inclined from the rear-end to tip-end direction of the sensor element 110, the effect that improves the responsiveness can be obtained if the opening area of the element-side opening 429 is smaller than the opening area of the outside opening 428.

While the above embodiment has been described with reference to the inner protection cover 130 serving as the gas flow channel forming member, the configuration is not limited thereto. For example, the inner protection cover 130 may include a member that is not the gas flow channel forming member, and the gas flow channel forming member may be part of the inner protection cover 130. More specifically, for example, the tip end portion 138 is configured to be a member that is not the second cylinder portion 136. In such a case, the first member 131 and the second cylinder portion 136 correspond to the gas flow channel forming member, and the gas flow channel forming member and the tip end portion 138 correspond to the inner protection cover 130. Alternatively, the gas flow channel forming member may be provided as a member that is independent from the inner protection cover 130.

While the above embodiment has been described with reference to the gas inlet port Ill that is open on the tip end surface of the sensor element 110 (the lower surface of the sensor element 110 in FIG. 2), the location of the opening is not limited thereto. For example, the gas inlet port 111 may be open on the side surface of the sensor element 110 (the left surface or the right surface of the sensor element 110 in FIG. 2).

While the above embodiment has been described with reference to the gas flow channel 127 formed as a cylindrical gap between the outer peripheral surface of the first cylinder portion 134 and the inner peripheral surface of the second cylinder portion 136, the gas flow channel 127 is not limited to a gap between two members. The gas flow channel 127 may be formed as a gap formed by three or more members. Alternatively, the gas flow channel forming member formed from a single member may have a through-hole formed therein, and the hole may serve as the gas flow channel 127.

Figure 11:
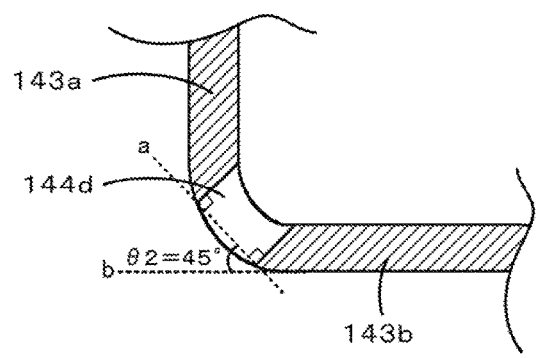
FIG. 11 is a partial cross-sectional view of a corner hole 144d.
Figure 12:
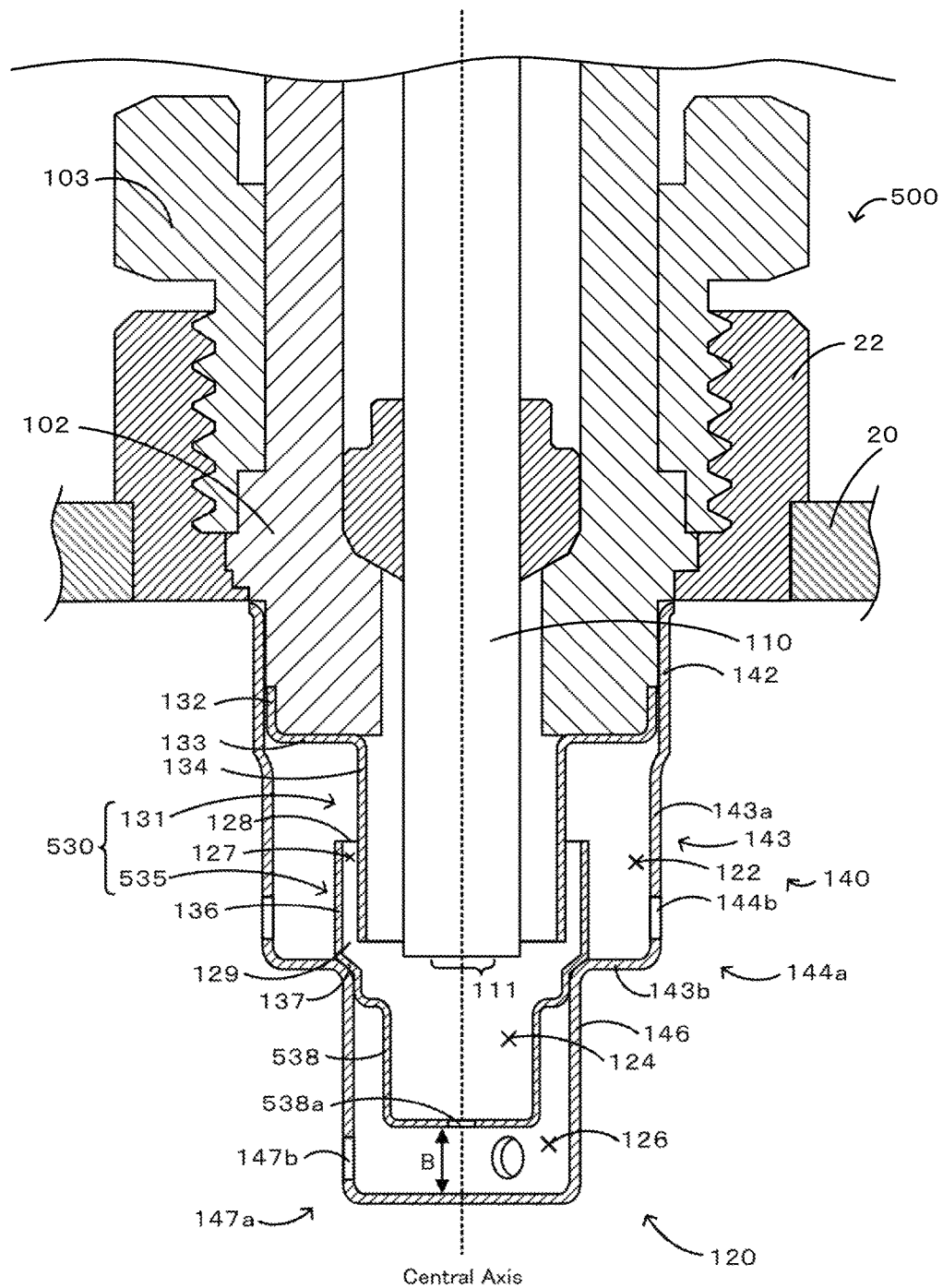
FIG. 12 is a vertical cross-sectional view of a gas sensor 500 according to a modification.

The shape of the outer protection cover 140 and the shapes, number, and arrangement of the first outer gas holes 144a and the second outer gas holes 147a according to the above-described embodiment are not limited to the above-described shapes, number, and arrangement. The shapes, number, and arrangement may be changed as needed. For example, the outer protection cover 140 need not have a bottomed cylindrical shape. More specifically, the tip end portion 146 may be bottomless, and the outer protection cover 140 may have a cylindrical shape. In addition, while the above embodiment has been described with reference to the first outer gas holes 144a including the horizontal holes 144b and the vertical holes 144c, the first outer gas holes 144a may include only the horizontal holes 144b or only the vertical holes 144c. Alternatively, in addition to or instead of the horizontal holes 144b and the vertical holes 144c, the first outer gas holes may be formed in a corner portion which is a boundary portion between the side portion 143a and the stepped portion 143b. For example, a corner hole 144d illustrated in FIG. 11 may be formed. The corner hole 144d is formed in a corner portion which is a boundary portion between the side portion 143a and the stepped portion 143b, and an angle θ2 formed by the external opening plane of the corner hole 144d (a line "a" in FIG. 11) and the bottom surface (the lower surface) (a line "b" in FIG. 11) of the stepped portion 143b is a value in the range from 10° to 80° (45° in FIG. 11). In addition, an angle formed by the inner peripheral surface and the external opening plane of the corner hole 144d is 90°. Similarly, the second outer gas holes 147a may include at least one of a horizontal hole, a vertical hole, and a corner hole. Like the outer protection cover 140, the shape of the inner protection cover 130 and the shape, number, and arrangement of the inner gas holes 138a may be changed as needed. For example, the inner protection cover 130 need not have a bottomed cylindrical shape. More specifically, the tip end portion 138 may be bottomless, and the inner protection cover 130 (the second member 135) may have a cylindrical shape. For example, the structure of an inner protection cover 530 illustrated in FIG. 12 may be employed. FIG. 12 is a vertical cross-sectional view of a gas sensor 500 according to a modification. The gas sensor 500 includes an inner protection cover 530. The inner protection cover 530 includes the first member 131 and a second member 535. Unlike the second member 135, the second member 535 does not include the tip end portion 138. Instead, the second member 535 includes a tip end portion 538. The tip end portion 538 is a bottomed cylindrical member having a diameter that is smaller than the diameter of the second cylinder portion 136. The tip end portion 538 is connected to the second cylinder portion 136 via the connection portion 137. The bottom surface of the tip end portion 538 has a circular inner gas hole 538a that allows the sensor element chamber 124 to communicate with the second gas chamber 126.

Figure 13:
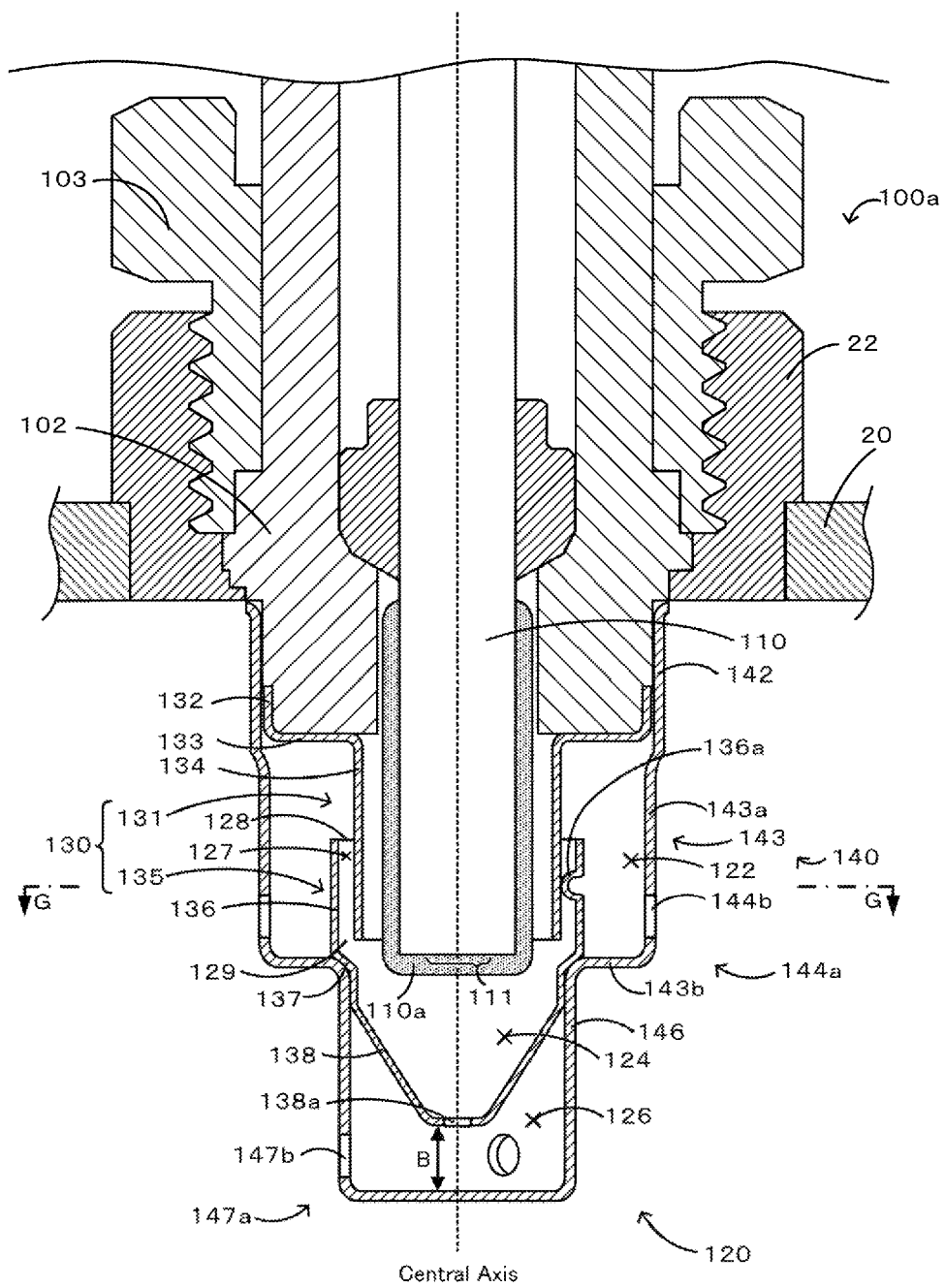
FIG. 13 is a vertical cross-sectional view of a gas sensor 100a according to a modification.
Figure 14:
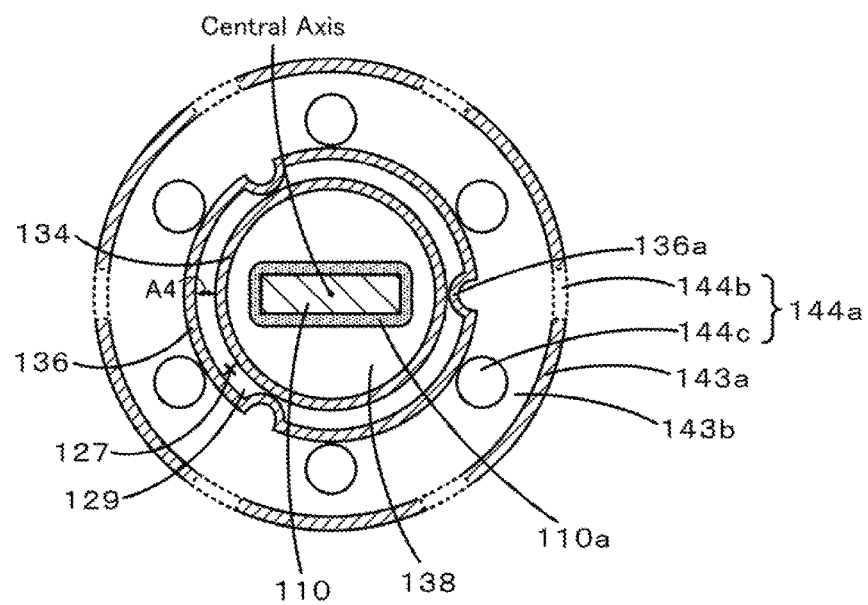
FIG. 14 is a cross-sectional view taken along a line G-G of FIG. 13.
Figure 15:
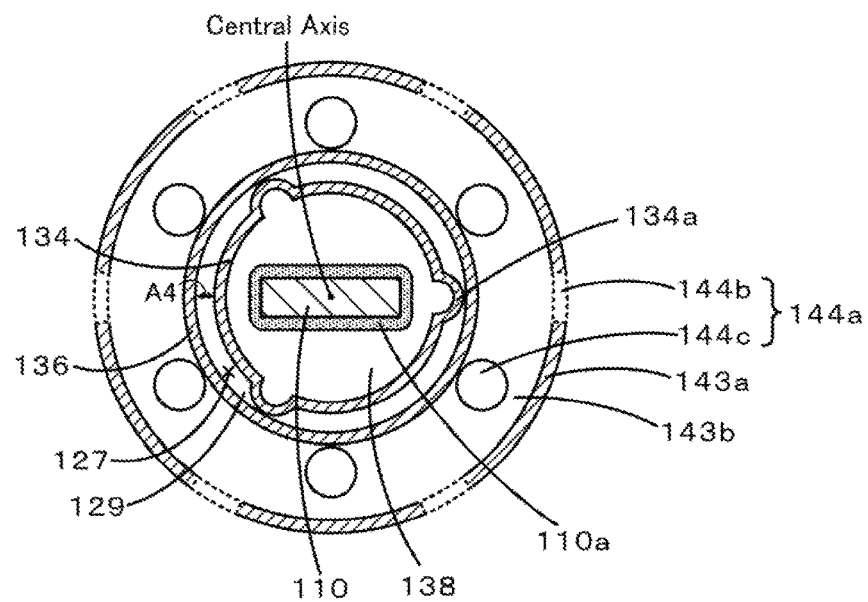
FIG. 15 is a cross-sectional view in a case of providing protruding portions 134a on a first cylinder portion 134.
Figure 16:
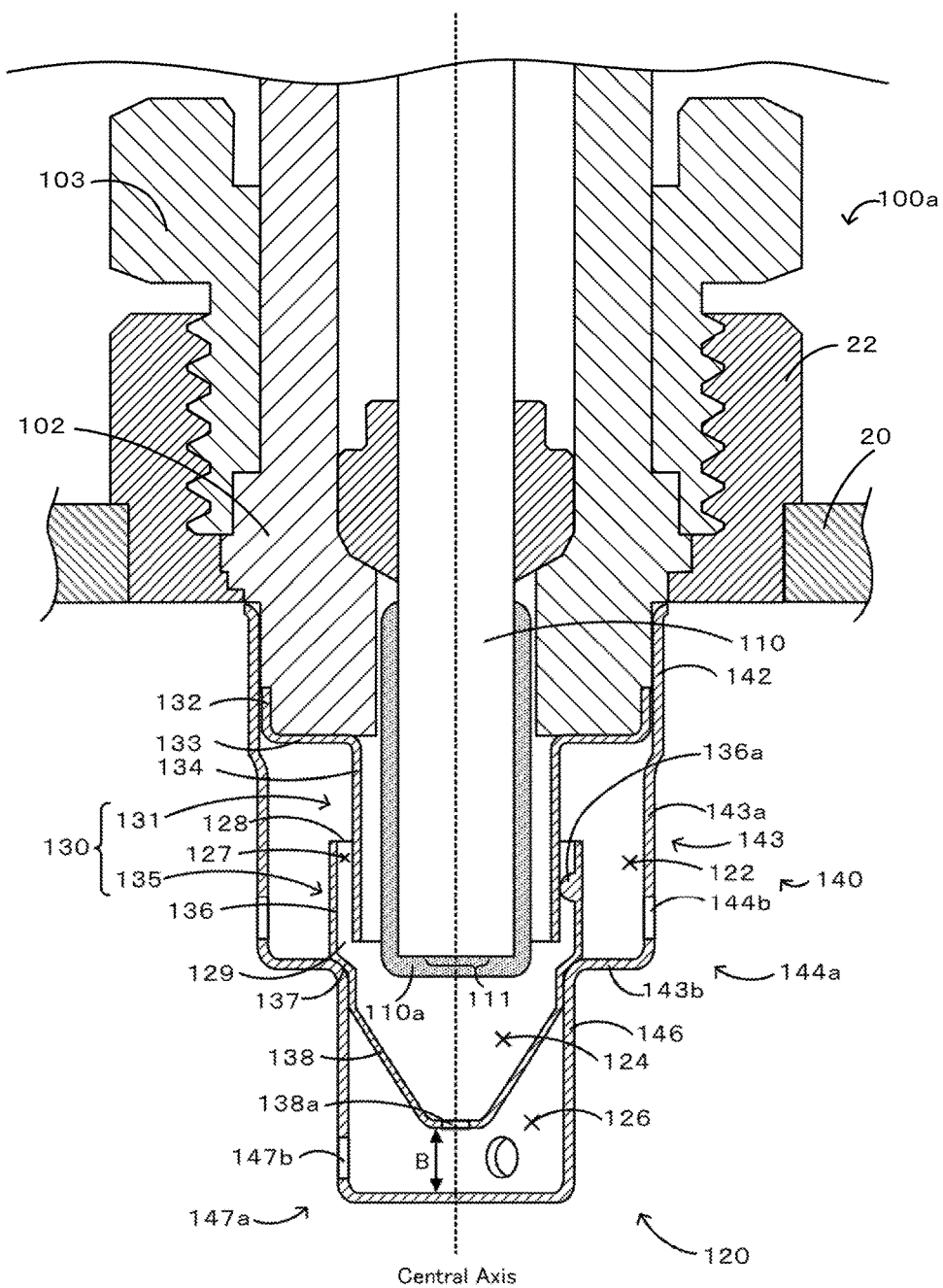
FIG. 16 is an illustration of protruding portions 136a according to a modification.

In the above-described embodiment, a protruding portion may be formed on the inner peripheral surface of the second cylinder portion 136. FIG. 13 is a vertical cross-sectional view of a gas sensor 100a according to a modification. FIG. 14 is a cross-sectional view taken along a line G-G of FIG. 13. The cross section of FIG. 13 is the same as that of FIG. 2. In the gas sensor 100a, a plurality of protruding portions 136a are formed on the inner peripheral surface of the second cylinder portion 136 so as to protrude toward the outer peripheral surface of the first cylinder portion 134 and be in contact with the outer peripheral surface. As illustrated in FIG. 14, three protruding portions 136a are formed at equal intervals in the circumferential direction of the inner peripheral surface of the second cylinder portion 136. Each of the protruding portions 136a is formed in a substantially hemispherical shape. By providing such protruding portions 136a, the positional relationship between the first cylinder portion 134 and the second cylinder portion 136 in the gas sensor 100a can be easily fixed by the protruding portions 136a. In addition, when, for example, the gas sensor 100a is assembled, the second member 135 can be attached to the first member 131 via the protruding portions 136a after the first member 131 is fixed to the housing 102. Accordingly, in the subsequent assembly process of the gas sensor 100a (e.g., in a process to attach the outer protection cover 140), falling off of the second member 135 from the first member 131 can be prevented and, thus, the assembly of the gas sensor 100a is facilitated. Note that it is desirable that the protruding portions 136a inwardly urge the outer peripheral surface of the first cylinder portion 134 in the radial direction. In this manner, the positional relationship between the first cylinder portion 134 and the second cylinder portion 136 can be more reliably fixed by the protruding portions 136a. The protruding portions 136a may be formed by, for example, pressing the outer peripheral surface of the second cylinder portion 136 toward the center to partially protrude the inner peripheral surface. Alternatively, the second cylinder portion 136 having the protruding portions 136a may be formed using a die in an integrated manner. Note that in FIG. 14, three protruding portions 136a are provided. However, it is only required that the positional relationship between the first cylinder portion 134 and the second cylinder portion 136 is fixed. The number of the protruding portions 136a may be two or four or more. Note that to easily stabilize the fixed positional relationship between the first cylinder portion 134 and the second cylinder portion 136, it is desirable that three or more protruding portions 136a be provided. In addition, the protruding portion may be formed on at least one of the outer peripheral surface of the first cylinder portion 134 and the inner peripheral surface of the second cylinder portion 136, and may be in contact with the other surface. For example, as illustrated in FIG. 15, a plurality of protruding portions 134a (three in FIG. 15) may be provided on the outer peripheral surface of the first cylinder portion 134 so as to protrude toward the inner peripheral surface of the second cylinder portion 136 and be in contact with the inner peripheral surface. In addition, a protruding portion may be formed on each of the outer peripheral surface of the first cylinder portion 134 and the inner peripheral surface of the second cylinder portion 136. In addition, in FIG. 13, part of the outer peripheral surface of the second cylinder portion 136 in which the protruding portion 136a is formed is inwardly concave. However, the structure is not limited thereto. For example, as illustrated in FIG. 16, part of the outer peripheral surface of the second cylinder portion 136 in which the protruding portion 136a is formed need not have a concave. Furthermore, the shape of the protruding portion is not limited to a hemispherical shape. The shape of the protruding portion may be any shape.

In addition, in the gas sensor 100a illustrated in FIG. 13 and FIG. 14, at least part of the surface of the sensor element 110 is covered by a porous protection layer 110a (also illustrated in FIG. 15 and FIG. 16). The porous protection layer 110a is formed on each of five of the six faces of the sensor element 110. Thus, the porous protection layer 110a covers almost entire surface of the sensor element 110 exposed to the inside of the sensor element chamber 124. More specifically, among the surface of the sensor element 110, the porous protection layer 110a covers the entire tip end surface (the lower surface in FIG. 13) having the gas inlet port 111 formed therein. In addition, the porous protection layer 110a covers a portion of each of the four faces connected to the tip end surface of the sensor element 110 (the upper, lower, right, and left faces of the sensor element 110 illustrated in FIG. 14) that is close to the tip end surface. The porous protection layer 110a covers the sensor element 110 to protect the covered portion. For example, the porous protection layer 110a prevents the sensor element 110 from cracking due to, for example, deposition of water contained in the measured gas. In addition, the porous protection layer 110a prevents an oil component, for example, contained in the measured gas from depositing on, for example, an electrode (not illustrated) on the surface of the sensor element 110. The porous protection layer 110a is formed from, for example, an alumina porous body, a zirconia porous body, a spinel porous body, a cordierite porous body, a titania porous body, or a magnesia porous body. The porous protection layer 110a is formed by using, for example, plasma spraying, screen printing, or dipping. Note that the porous protection layer 110a also covers the gas inlet port 111. However, since the porous protection layer 110a is a porous body, the measured gas can reach the gas inlet port 111 by flowing through the inside of the porous protection layer 110a. Note that in addition to the gas sensor 100a, in other gas sensors, such as the gas sensor 100 according to the above-described embodiment, the surface of the sensor element 110 may be covered by a porous protection layer.

Figure 17:
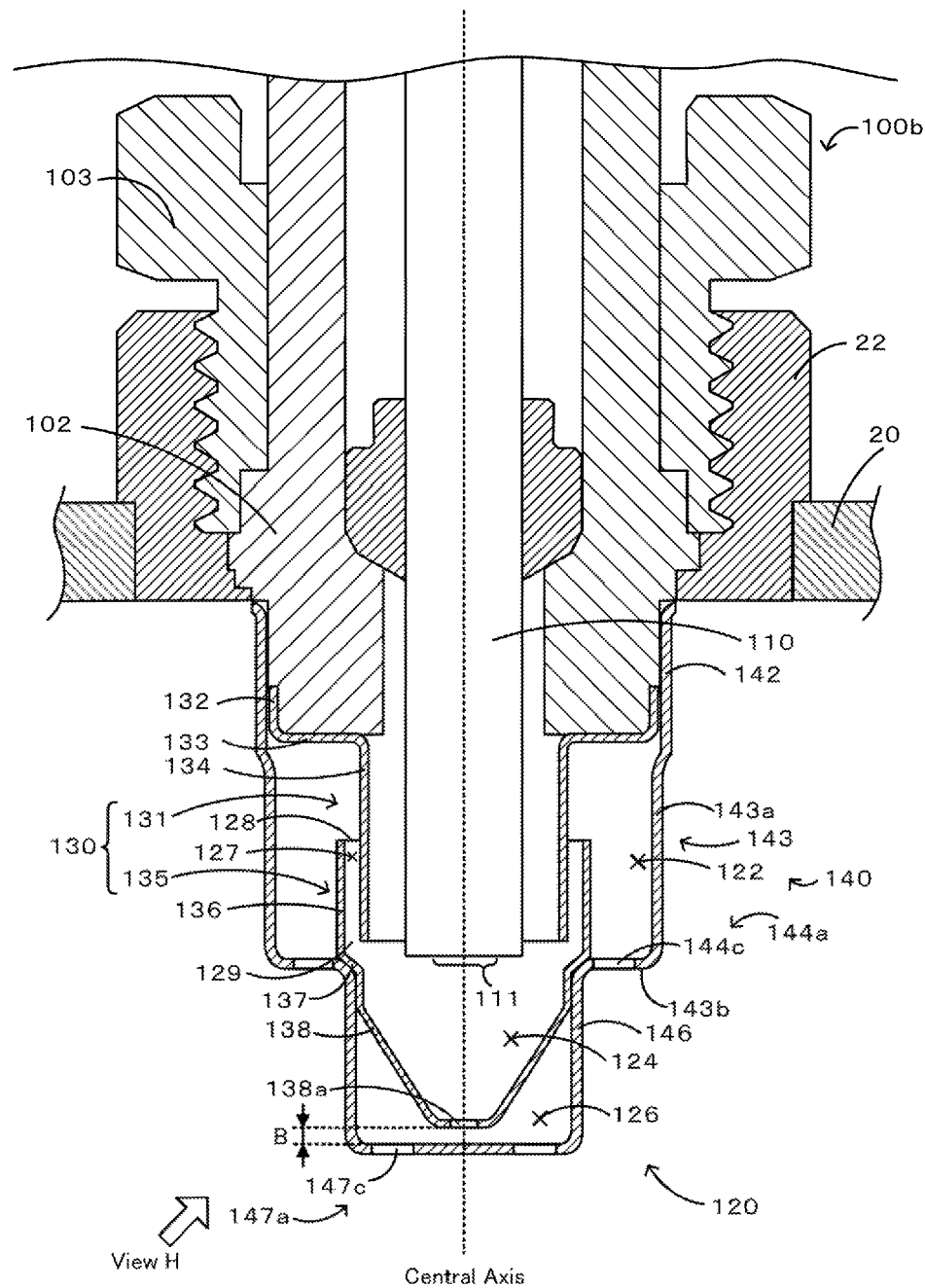
FIG. 17 is a vertical cross-sectional view of the gas sensor 100b according to a modification
Figure 18:
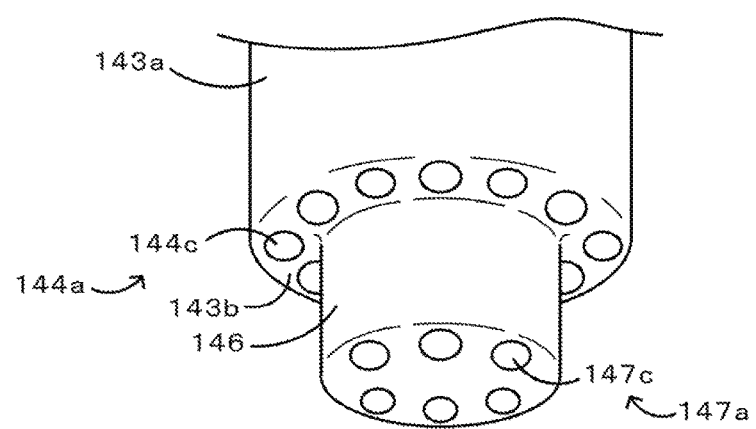
FIG. 18 is a view on Arrow H of FIG. 17.

In the above-described embodiment, the length of the tip end portion 146 in the axial direction may be decreased so that the distance B is smaller than that in FIG. 2. FIG. 17 is a vertical cross-sectional view of the gas sensor 100b according to a modification in this case. FIG. 18 is a view on Arrow H of FIG. 17. Note that FIG. 17 illustrates the cross section that is the same as that of FIG. 2. In this gas sensor 100b, the length of the tip end portion 146 in the axial direction is short and, thus, the distance B is small. The distance B may be set to, for example, 0.6 mm, but is not necessarily limited thereto. In addition, in this gas sensor 100b, twelve vertical holes 144c are formed as the first outer gas holes 144a at equal intervals, and six vertical holes 147c are formed as the second outer gas holes 147a at equal intervals. The horizontal holes 144b and the horizontal holes 147b illustrated in FIG. 2 are not formed in the gas sensor 100b.

EXAMPLES

Experimental Example 1

The gas sensor 100 illustrated in FIGS. 1 to 5 is used as Experimental Example 1. More specifically, the first member 131 of the inner protection cover 130 is 0.3 mm in thickness and is 10.0 mm in length in the axial direction. The large-diameter portion 132 is 1.8 mm in length in the axial direction. The external diameter of the large-diameter portion is 8.2 mm. The first cylinder portion 134 is 8.1 mm in length in the axial direction. The external diameter of the first cylinder portion 134 is 7.7 mm. The second member 135 is 0.3 mm in thickness and is 11.5 mm in length in the axial direction. The second cylinder portion 136 is 4.5 mm in length in the axial direction. The internal diameter of the second cylinder portion 136 is 8.7 an. The tip end portion 138 is 4.9 mm in length in the axial direction. The diameter of the bottom surface of the tip end portion 138 is 2.5 mm. For the gas flow channel 127, the distance A1 is set to 0.5 mm, the distance A2 is set to 1.9 mm, the distance A3 is set to 2.8 mm, each of the distances A4 and A5 is set to 0.5 mm, the distance A6 is set to 1.6 mm, and the distance L is set to 4 mm. The inner gas hole 138a is a vertical hole having a diameter of 1.5 mm. The inner gas hole 138a is formed at the central point of the bottom surface of the tip end portion 138. The outer protection cover 140 is 0.4 mm in thickness and is 24.2 mm in length in the axial direction. The large-diameter portion 142 is 6.1 mm in length in the axial direction. The external diameter of the large-diameter portion 142 is 15.2 mm. The body portion 143 is 8.5 mm in length in the axial direction. The external diameter of the body portion 143 is 14.6 ram. The tip end portion 146 is 9.6 mm in length in the axial direction. The external diameter of the tip end portion 146 is 8.7 mm. The first outer gas holes 144a are formed from six horizontal holes 144b each having a diameter of 1 mm and six vertical holes 144c each having a diameter of 1 mm. The horizontal holes 144b and the vertical holes 144c are alternately arranged at equal intervals (the angle formed by the neighboring holes is 30°). The second outer gas holes 147a are formed from three horizontal holes 147b each having a diameter of 1 mm and three vertical holes 147c each having a diameter of 1 mm. The horizontal holes 147b and the vertical holes 147c are alternately arranged at equal intervals (the angle formed by the neighboring holes is 60°). The distance B is set to 2.7 mm. In addition, the sensor element 110 of the gas sensor 100 is 4 mm in width (the length in the right-left direction of FIG. 2) and is 1.5 mm in thickness (the length in a direction perpendicular to the plane of FIG. 2). The sensor element 110 of the gas sensor 100 detects the oxygen concentration. Note that the gas sensor 100 having the gas inlet port 111 that is open on the tip end surface of the sensor element 110 is used.

Experimental Example 2

Figure 19:
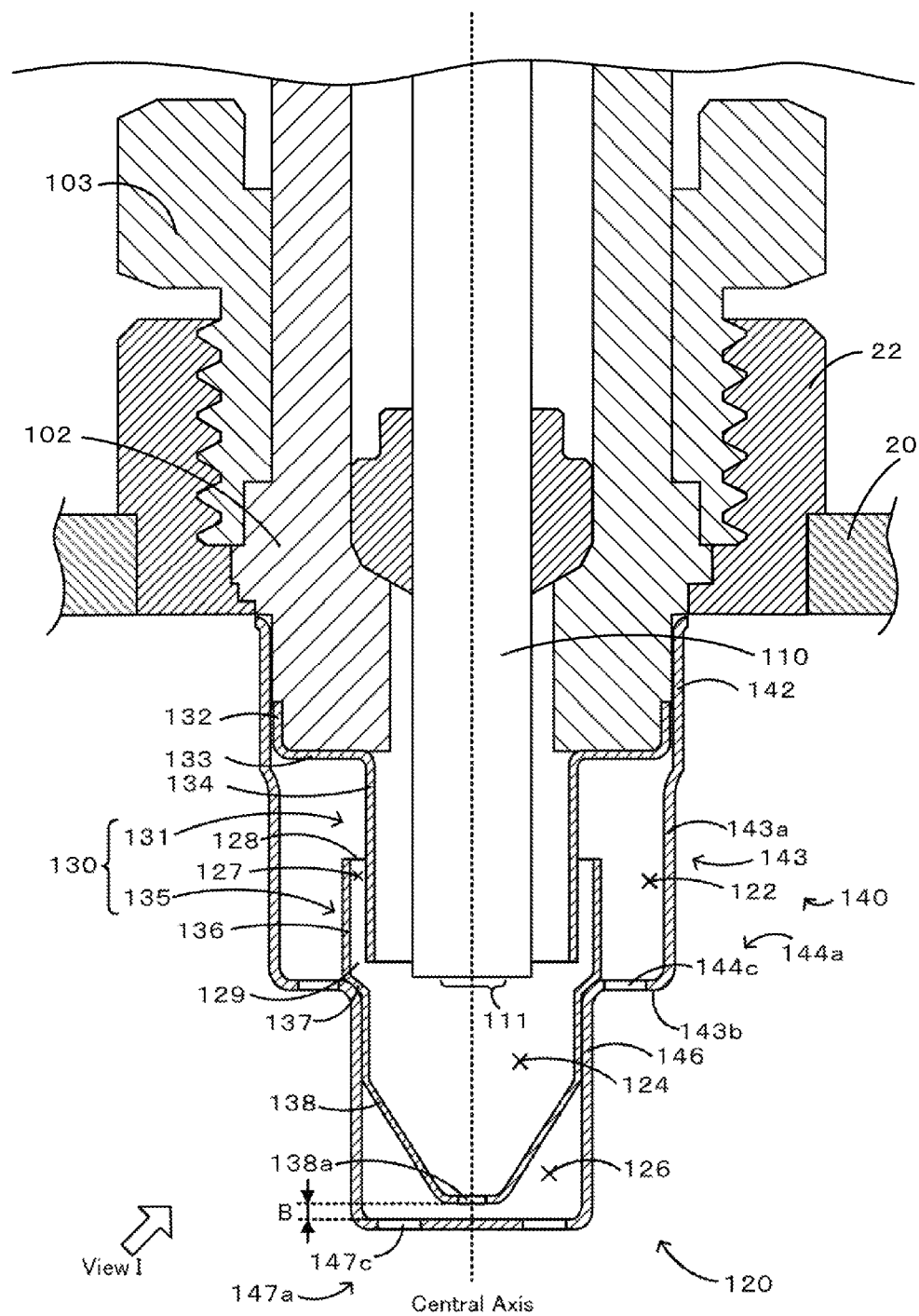
FIG. 19 is a cross-sectional view of the gas sensor of Experimental Example 2.
Figure 20:
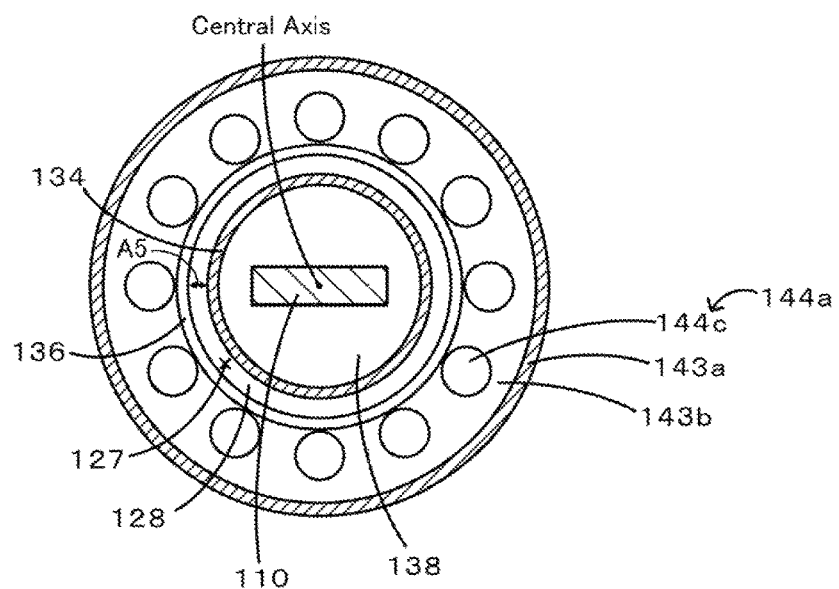
FIG. 20 is a cross-sectional view of the gas sensor of Experimental Example 2.
Figure 21:
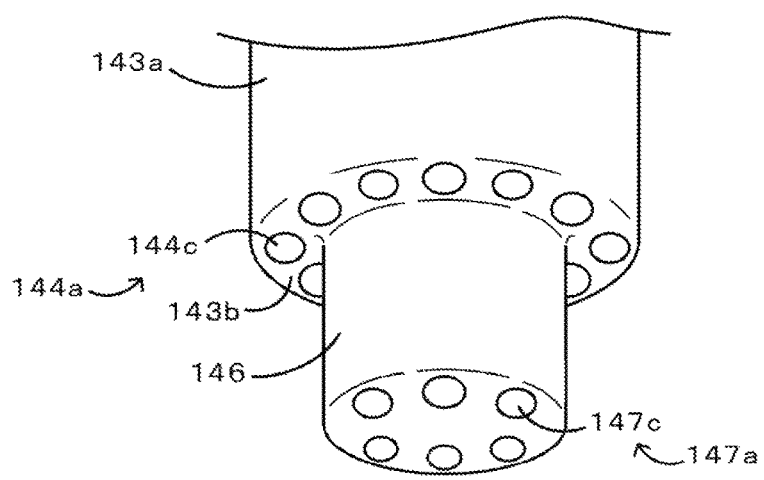
FIG. 21 is a view on Arrow I of FIG. 19.

The following gas sensor is used as Experimental Example 2. That is, as the first outer gas holes 144a, 12 vertical holes 144c each having a diameter of 1 mm are formed at equal intervals. As the second outer gas holes 147a, six vertical holes 147c each having a diameter of 1 mm are formed at equal intervals. The length of the tip end portion 138 in the axial direction is increased so that the distance B is 0.6 mm. The other values are the same as those of Experimental Example 1. Note that for the gas flow channel 127, the distance A1 is set to 0.5 mm, the distance A2 is set to 1.9 mm, the distance A3 is set to 4.6 mm, each of the distances A4 and A5 is set to 0.5 mm, the distance A6 is set to 1.6 mm, and the distance L is set to 4 mm. Note that in Experimental Example 2, the distance A3 represents the distance between the end portion of the vertical holes 144c adjacent to the rear end of the sensor element (the upper side of FIG. 19) and the outside opening 128 in the vertical direction of FIG. 19. FIG. 19 and FIG. 20 are cross-sectional views of the gas sensor of Experimental Example 2. Note that the cross sections of FIG. 19 and FIG. 20 are the same as those of FIG. 2 and FIG. 4, respectively. FIG. 21 is a view on Arrow I of FIG. 19.

Experimental Example 3

The gas sensor 300 illustrated in FIGS. 8 and 9 is used as Experimental Example 3. The outer protection cover 140 has the same configuration as that of Experimental Example 2. The second member 135 of the inner protection cover 330 is the same as that of Experimental Example 2. The distance B is set to 0.6 mm. The first member 331 has six concave portions 334a formed therein at equal intervals. Four gas flow channels 327 each having a cross-sectional area of 2.7 mm$^2$ that is perpendicular to the tip end to rear end direction of the sensor element 110 are formed. For the gas flow channel 327, the distance A1 is set to 0.5 mm, the distance A2 is set to 1.3 mm, the distance A3 is set to 2.8 mm, the distance A6 is set to 1.0 mm, and the distance L is set to 4 mm. In Experimental Example 3, since the first cylinder portion 334 is the closest to the sensor element 110, the distance A6 represents the smallest distance between the sensor element 110 and the inner peripheral surface of the first cylinder portion 334.

Experimental Example 4

The gas sensor 200 illustrated in FIGS. 6 and 7 is used as Experimental Example 4. The outer protection cover 140 has a configuration that is the same as that of Experimental Example 1. The inner protection cover 230 is 0.3 mm in thickness and is 17.7 mm in length in the axial direction. The large-diameter portion 132 is 1.8 mm in length in the axial direction. The external diameter of the large-diameter portion is 8.2 mm. The cylinder portion 234 is 9.3 mm in length in the axial direction. The external diameter of the cylinder portion 234 is 8.2 mm. The tip end portion 138 is 4.9 mm in length in the axial direction. The diameter of the bottom surface of the tip end portion 138 is 2.5 mm. The distance B is set to 2.7 mm. Six rectangular through-holes each having an external opening area of 0.479 mm$^2$ are formed in the cylinder portion 234 at equal intervals to serve as the gas flow channel 227. The distance A1 is set to 0.5 mm, and the distance A2 (=the distance A6) is set to 1.8 mm. In addition, each of the gas flow channel 227 has a corresponding regulation member 227a. The formed angle θ1 is set to 380.

Experimental Example 5

Figure 22:
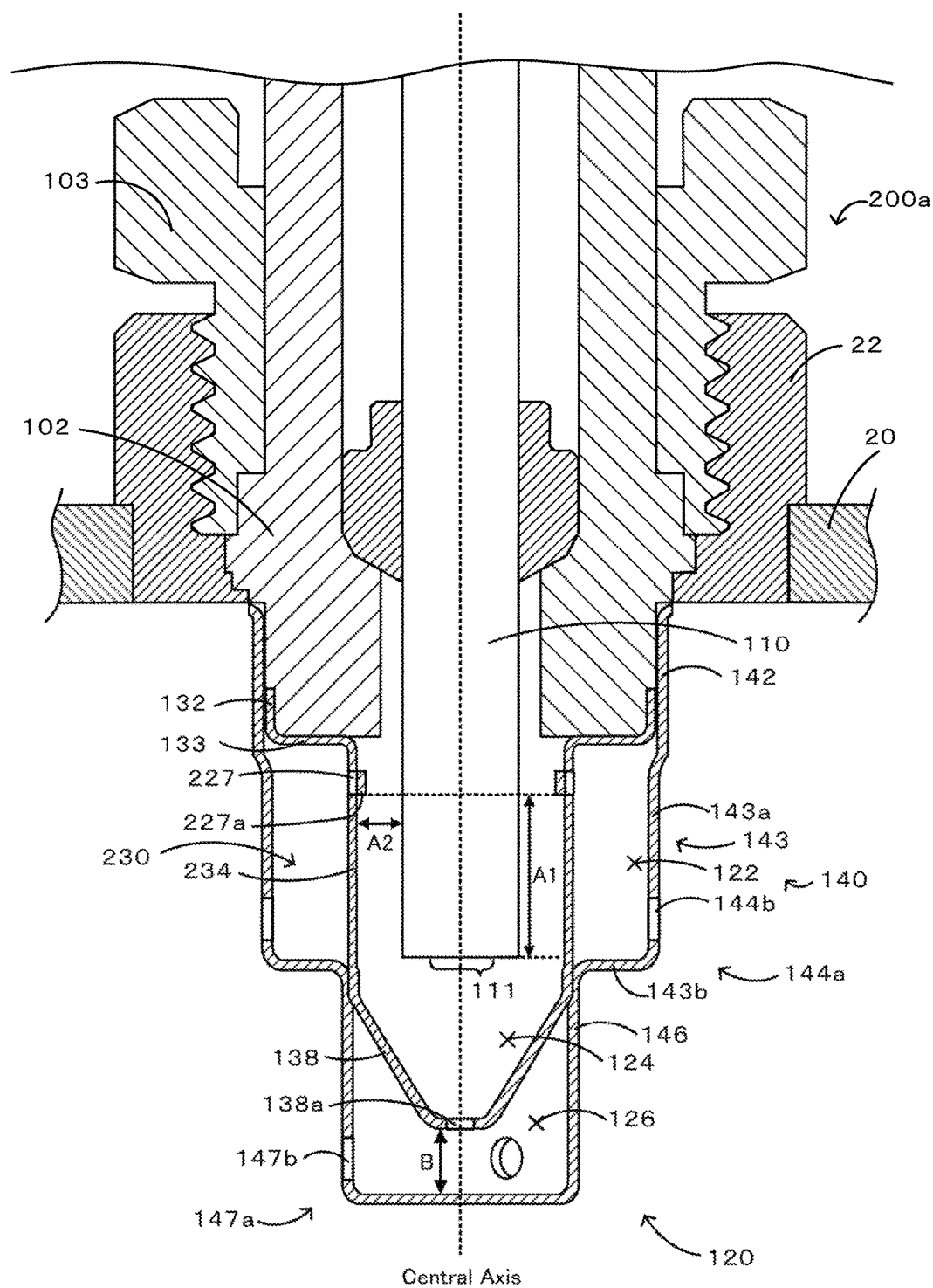
FIG. 22 is a vertical cross-sectional view of the gas sensor 200a of Experimental Example 5.

A gas sensor 200a illustrated in FIG. 22 is used as Experimental Example 5. In the gas sensor 200a illustrated in FIG. 22, the gas flow channels 227 and the regulation members 227a are formed at positions closer to the rear end of the sensor element 110 than in Experimental Example 4 (the distance A1 is increased), the diameter of the inner gas hole 138a is decreased, the first outer gas holes 144a do not include the vertical hole 144c and includes six horizontal holes 144b each having a diameter of 1 mm and formed at equal intervals, and the second outer gas holes 147a do not include the vertical hole 147c and includes six horizontal holes 147b each having a diameter of 1 mm and formed at equal intervals. The other values are the same as those of the gas sensor 200 (Experimental Example 4) illustrated in FIGS. 6 and 7. Note that for the outer protection cover 140, the distance A1 is set to 6.0 mm. The distance A2 (the distance from the sensor element 110 to the inner peripheral surface of the cylinder portion 234, which is equal to the distance A6) is set to 1.8 mm, and the diameter of the inner gas hole 138a is set to 1 mm.

Experimental Example 6

Figure 23:
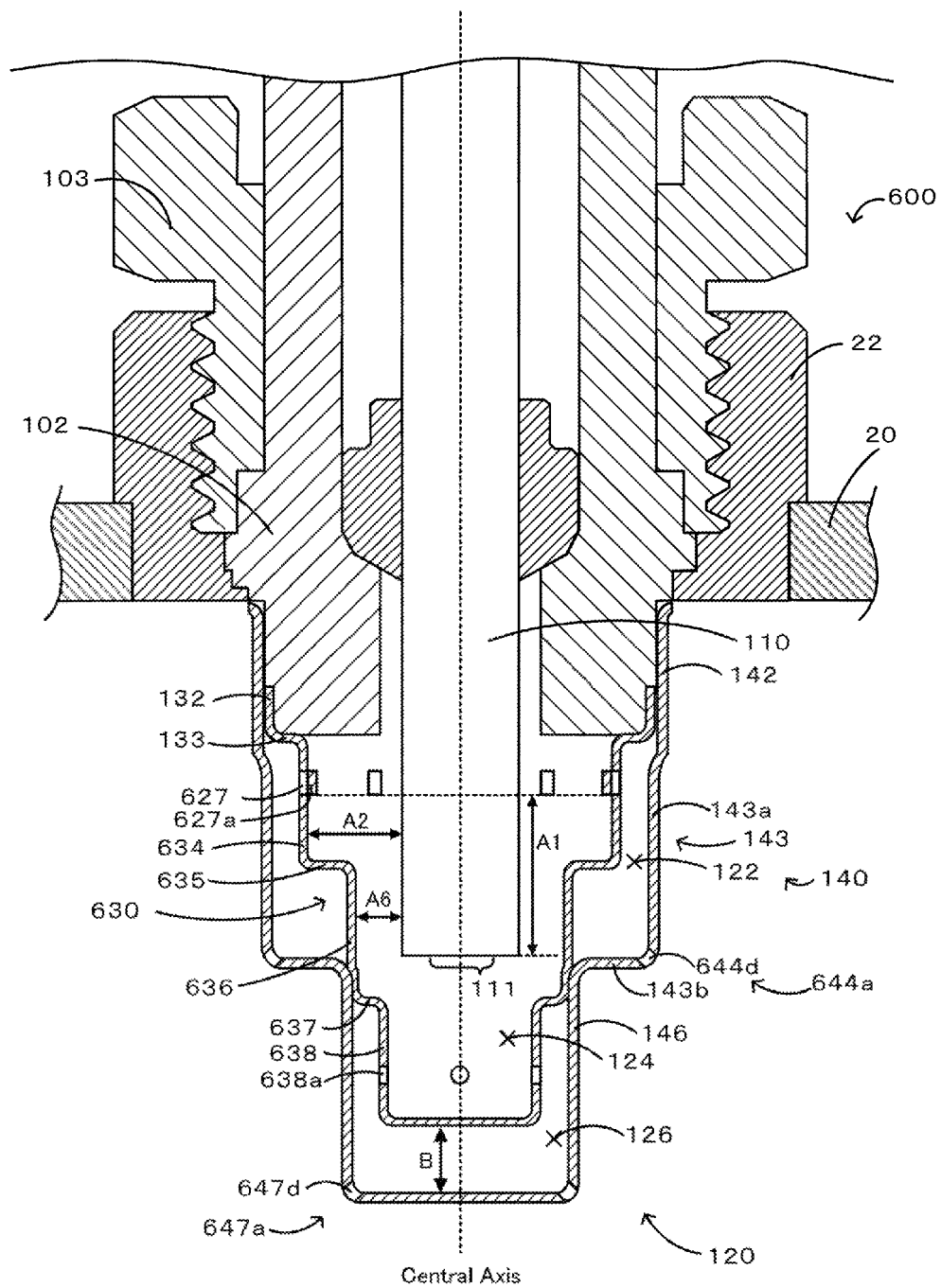
FIG. 23 is a vertical cross-sectional view of the gas sensor 600 of Experimental Example 6.

A gas sensor 600 illustrated in FIG. 23 is used as Experimental Example 6. Note that in FIG. 23, constituent elements similar to those of the gas sensor 100 are identified with the same reference numerals, and detailed description of the constituent elements is not repeated. The gas sensor 600 includes an inner protection cover 630 instead of the inner protection cover 130. The inner protection cover 630 includes the large-diameter portion 132, a cylindrical first body portion 634 having a diameter smaller than that of the large-diameter portion 132, a cylindrical second body portion 636 having a diameter smaller than that of the first body portion 634, and a bottomed cylindrical tip end portion 638 having a diameter smaller than that of the second body portion 636. The large-diameter portion 132 is connected to the first body portion 634 using the stepped portion 133. In addition, the inner protection cover 630 includes a stepped portion 635 that connects the first body portion 634 to the second body portion 636 and a stepped portion 637 that connects the second body portion 636 to the tip end portion 638. Note that the central axes of the large-diameter portion 132, the first body portion 634, the second body portion 636, and the tip end portion 638 are the same. The first body portion 634 and the second body portion 636 are located so as to cover the side surface of the sensor element 110. Like the gas flow channel 227 illustrated in FIG. 6, the first body portion 634 has six through-holes formed therein. Each of the through-holes has a rectangular opening. The inside of each of the holes serves as a gas flow channel 627. The gas flow channels 627 are formed along the circumference of the first body portion 634 at equal intervals. The gas flow channels 627 are formed as flow channels extending in a direction perpendicular to the tip end to rear end direction of the sensor element 110 (the right-left direction of FIG. 23). In addition, the gas flow channels 627 are formed as flow channels extending in a direction toward the central axis of the first body portion 634 (the radial direction) as viewed from a cross section perpendicular to the central axis. Like the regulation members 227a, the first body portion 634 has six plate-like regulation members 627a formed therein at equal intervals. The regulation members 627a regulate the flow of the measured gas flowing into the sensor element chamber 124 through the gas flow channels 627. The regulation members 627a are in one-to-one correspondence with the gas flow channels 627. Each of the regulation members 627a is formed so as to be located between a corresponding gas flow channel 627 and the sensor element 110. In addition, the regulation members 627a are formed so as to be rotationally symmetrical (sixfold rotationally symmetrical). The side surface of the tip end portion 638 has four inner gas holes 638a formed therein at equal intervals. The inner gas holes 638a allow the sensor element chamber 124 to communicate with the second gas chamber 126. The inner protection cover 630 is 0.3 mm in thickness and is 17.7 mm in length in the axial direction. The large-diameter portion 132 is 1.8 mm in length in the axial direction. The external diameter of the large-diameter portion 132 is 14.1 mm. The first body portion 634 is 5.4 mm in length in the axial direction. The external diameter of the first body portion 634 is 11.8 mm. The second body portion 636 is 5.6 mm in length in the axial direction. The external diameter of the second body portion 636 is 8.2 mm. The tip end portion 638 is 4.9 mm in length in the axial direction. The external diameter of the tip end portion 638 is 5.9 mm. The external opening area of the gas flow channel 627 is 0.396 mm. In addition, the distance A1 is set to 6.2 mm, and the distance A2 is set to 3.6 mm. Note that since the element-side opening of the gas flow channel 627 is located in the inner peripheral surface of the first body portion 634, the distance between the sensor element 110 and the inner peripheral surface of the first body portion 634 is the distance A2. Furthermore, the distance A6 is set to 1.8 mm. Note that in Experimental Example 6, since the second body portion 636 is the closest to the sensor element 110, the smallest distance between the sensor element 110 and the inner peripheral surface of the second body portion 636 is the distance A6. The angle θ1 formed by the regulation surface of each of the regulation members 627a and the outside opening plane of each of the gas flow channels 627 is set to 38°. The inner gas holes 638a are formed as horizontal holes each having a diameter of 1 mm. The outer protection cover 140 has a configuration that is the same as that of Experimental Example 1. However, instead of the first outer gas holes 144a and the second outer gas holes 147a, first outer gas holes 644a include six corner holes 644d each having a diameter of 1 mm and formed at equal intervals, and second outer gas holes 647a include six corner holes 647d each having a diameter of 1.2 mm and formed at equal intervals. The angle θ2 formed by the external opening plane of each of the corner hole 644d and the corner hole 647d and the bottom surface (the stepped portion 143b, the bottom surface of the tip end portion 146) is set to 45°. The distance B is set to 2.7 mm.

Experimental Example 7

The following gas sensor is configured as Experimental Example 7. That is, six vertical holes 144c each having a diameter of 1 mm are formed at equal intervals as the first outer gas holes 144a, and six vertical holes 147c each having a diameter of 1 mm are formed at equal intervals as the second outer gas holes 147a. The other values are the same as those of Experimental Example 5.

Experimental Example 8

The following gas sensor is configured as Experimental Example 8. That is, the diameter of each of the inner gas holes 138a is set to 1.5 mm. The other values are the same as those of Experimental Example 5.

Experimental Example 9

To form the first outer gas holes 644a, instead of the corner holes 644d, six horizontal holes 144b each having a diameter of 1 mm and six vertical holes 144c each having a diameter of 1 mm are alternately formed at equal intervals (the angle formed by neighboring holes is 30°). In addition, to form the second outer gas holes 647a, instead of the corner holes 647d, three horizontal holes 147b each having a diameter of 1 mm and three vertical holes 147c each having a diameter of 1 mm are alternately formed at equal intervals (the angle formed by neighboring holes is 60°). That is, to form the first outer gas holes 644a and the second outer gas holes 647a, holes that are similar to the first outer gas holes 144a and the second outer gas holes 147a of Experimental Example 1 are formed. A gas sensor having a configuration that is the same as in Experimental Example 6 except for the above-described configuration is used as Experimental Example 9.

Experimental Example 10

The first outer gas holes 144a are formed so as to include six horizontal holes 144b each having a diameter of 1 mm and six vertical holes 144c each having a diameter of 1 mm alternately formed at equal intervals (the angle formed by neighboring holes is 30°). The second outer gas holes 147a are formed so as to include three horizontal holes 147b each having a diameter of 1 mm and three vertical holes 147c each having a diameter of 1 mm alternately formed at equal intervals (the angle formed by neighboring holes is 60°). A gas sensor having a configuration that is the same as in Experimental Example 5 except for the above-described configuration is used as Experimental Example 10.

Experimental Example 11

Figure 24:
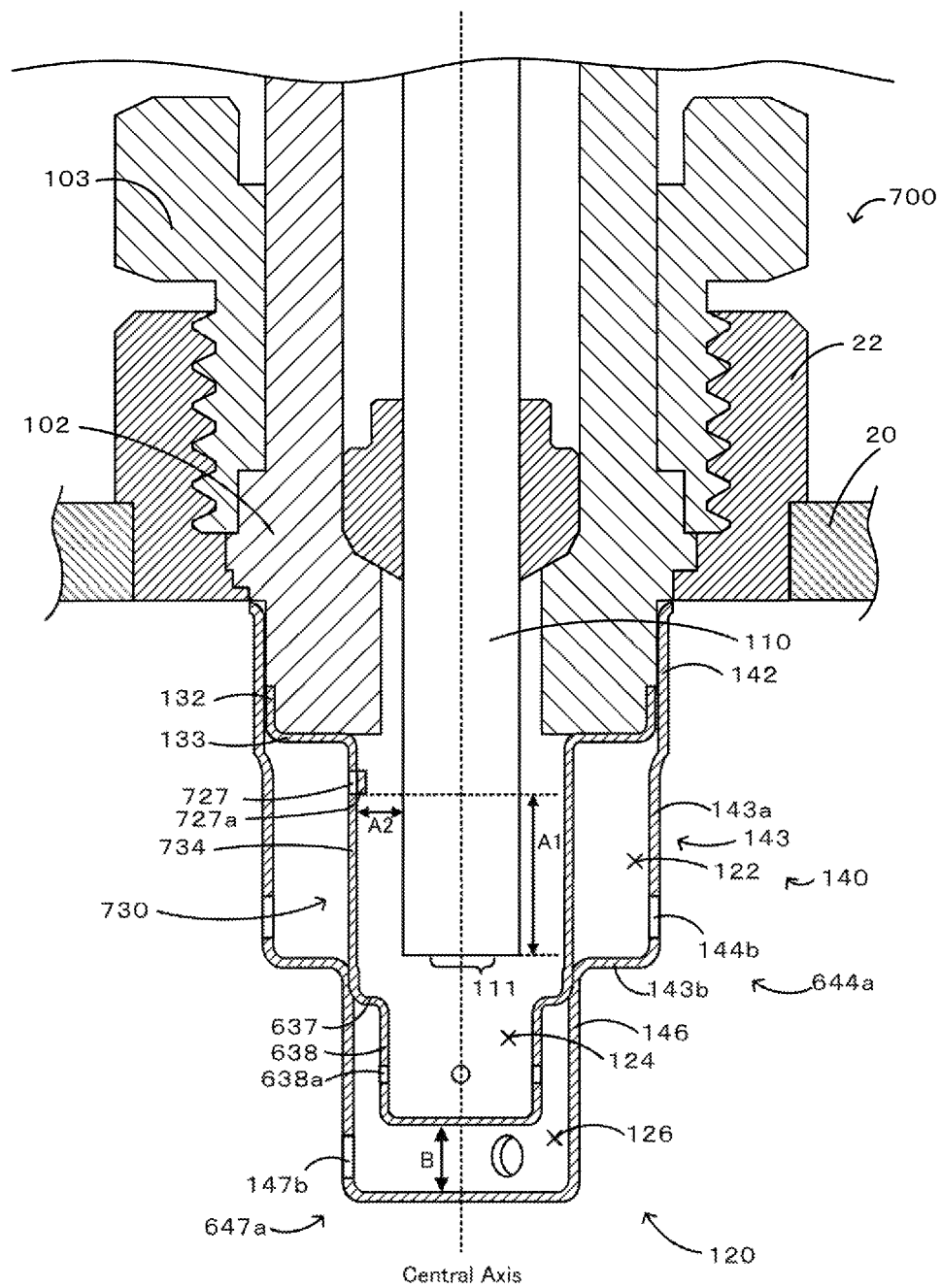
FIG. 24 is a vertical cross-sectional view of the gas sensor 700 of Experimental Example 11.

A gas sensor 700 illustrated in FIG. 24 is used as Experimental Example 11. Note that in FIG. 24, constituent elements similar to those of the gas sensor 600 in FIG. 23 are identified with the same reference numerals, and detailed description of the constituent elements is not repeated. The gas sensor 700 includes an inner protection cover 730. Unlike the inner protection cover 630, the inner protection cover 730 does not include the first body portion 634, the stepped portion 635, and the second body portion 636. Instead, the inner protection cover 730 includes a body portion 734. The body portion 734 is connected to the large-diameter portion 132 via the stepped portion 133 and is connected to the tip end portion 638 via the stepped portion 637. That is, the shape of the inner protection cover 730 is the same as the shape of the inner protection cover 630 illustrated in FIG. 23 in which the internal diameter of the first body portion 634 is made to be the same as the internal diameter of the second body portion 636. Like the gas flow channels 627 and the regulation members 627a, the body portion 734 has gas flow channels 727 and regulation members 727a formed at equal intervals. However, the number of the gas flow channels 727 is three, and the number of the regulation members 727a is three. The distance A1 is set to 6.2 un, the distance A2 (=the distance A6) is set to 1.8 mm, and the distance B is set to 2.7 ram. Note that in Experimental Example 11, since the body portion 734 is the closest to the sensor element 110 and the element-side openings of the gas flow channels 727 are located in the inner peripheral surface of the body portion 734, the smallest distance between the sensor element 110 and the inner peripheral surface of the body portion 734 is the distance A2 (=the distance A6). In addition, as in Experimental Example 9, the outer protection cover 140 includes the first outer gas holes 644a formed from six horizontal holes 144b each having a diameter of 1 mm and six vertical holes 144c each having a diameter of 1 m and the second outer gas holes 647a formed from three horizontal holes 147b each having a diameter of 1 mm and three vertical holes 147c each having a diameter of 1 mm.

Experimental Example 12

The following gas sensor is configured as Experimental Example 12. That is, the internal diameter of the body portion 734 is changed so that the distance A2 (=the distance A6) is 2.5 mm. The other values are the same as those of Experimental Example 11.

Experimental Example 13

A gas sensor of Experimental Example 13 is configured by changing the following values of the gas sensor of Experimental Example 1. More specifically, by increasing the internal diameter of the second cylinder portion 136, each of the distance A4 and the distance A5 is set to 1.0 m. By increasing the length of the second cylinder portion 136 in the axial direction in a direction toward the rear end of the sensor element 110 (the upward direction of FIG. 2), the distance L is set to 4.3 mm, and the distance A3 is set to 3.1 mm.

Experimental Example 14

A gas sensor of Experimental Example 14 is configured by changing the following values of the gas sensor of Experimental Example 1. More specifically, by increasing the external diameters of the first cylinder portion 134 and the second cylinder portion 136 without changing the values of the distance A4 and the distance A5, the distance A2 is set to 2.4 min, and the distance A6 is set to 2.1 mm. By increasing the length of the second cylinder portion 136 in the axial direction in a direction toward the rear end of the sensor element 110 (the upward direction of FIG. 2), the distance L is set to 4.3 mm, and the distance A3 is set to 3.1 mm.

Experimental Example 15

A gas sensor of Experimental Example 15 is configured by changing the following values of the gas sensor of Experimental Example 13. More specifically, the position at which the sensor element 110 is attached is shifted in a direction toward the tip end of the sensor element 110 (the downward direction of FIG. 2) so that the distance A1 is 1.0 mm.

Experimental Example 16

A gas sensor of Experimental Example 16 is configured by changing the following values of the gas sensor of Experimental Example 13. More specifically, the position at which the sensor element 110 is attached is shifted in a direction toward the rear end of the sensor element 110 (the upward direction of FIG. 2) so that the distance A1 is −0.6 mm.

Experimental Example 17

A gas sensor of Experimental Example 17 is configured by changing the following values of the gas sensor of Experimental Example 13. More specifically, the length of the second cylinder portion 136 in the axial direction is increased in a direction toward the rear end of the sensor element 110 (the upward direction of FIG. 2) so that the distance L is 5.3 mm and the distance A3 is 4.1 mm.

Experimental Example 18

A gas sensor of Experimental Example 18 is configured by changing the following values of the gas sensor of Experimental Example 13. More specifically, the length of the second cylinder portion 136 in the axial direction is decreased so that the distance L is 3.3 mm and the distance A3 is 2.1 ram.

Experimental Example 19

A gas sensor of Experimental Example 19 is configured by changing the following values of the gas sensor of Experimental Example 2. More specifically, the diameters of the vertical holes 144c and the vertical holes 147c are set to 1.2 mm. The length of the second cylinder portion 136 in the axial direction is increased so that the distance L is 4.3 mm and the distance A3 is 4.9 mm.

Experimental Example 20

A gas sensor of Experimental Example 20 is configured by changing the following values of the gas sensor of Experimental Example 1. More specifically, the length of the second cylinder portion 136 in the axial direction is increased in a direction toward the rear end of the sensor element 110 (the upward direction of FIG. 2) so that the distance L is 4.3 mm and the distance A3 is 3.1 mm.

Experimental Example 21

The gas sensor 100b illustrated in FIG. 17 and FIG. 18 is used as Experimental Example 21. More specifically, a gas sensor of Experimental Example 21 is configured by changing the following values of the gas sensor of Experimental Example 1. That is, as the first outer gas holes 144a, twelve vertical holes 144c each having a diameter of 1 mm are formed at equal intervals. As the second outer gas holes 147a, six vertical holes 147c each having a diameter of 1 mm are formed at equal intervals. In addition, the length of the tip end portion 146 in the axial direction is decreased so that the distance B is 0.6 mm. The length of the second cylinder portion 136 in the axial direction is increased in a direction toward the rear end of the sensor element 110 (the upward direction of FIG. 2) so that the distance L is 4.3 mm and the distance A3 is 4.9 mm. Note that the distance A3 of Experimental Example 21 is defined as the distance between the end portion of the vertical hole 144c adjacent to the rear end of the sensor element (the upper side of FIG. 17) and the outside opening 128 in the vertical direction of FIG. 17.

Experimental Example 22

A gas sensor of Experimental Example 22 is configured by changing the following values of the gas sensor of Experimental Example 3. More specifically, the length of the second cylinder portion 136 in the axial direction is increased in the direction toward the rear end of the sensor element 110 (the upward direction of FIG. 2) so that the distance L is 4.3 mm and the distance A3 is 3.1 mm.

[Evaluation Test 1]

The gas sensors of Experimental Examples 1 to 22 were evaluated in terms of the heat-retaining properties and the responsiveness of gas concentration detection of the sensor element. More specifically, the evaluation was conducted as follows.

That is, each of the gas sensors of Experimental Examples 1 to 22 was attached to a pipe in the same manner as illustrated in FIG. 1A and FIG. 1B. Note that the pipe was completely filled with air. The pipe was kept with the inside under windless conditions for 310 seconds. Thereafter, the measured gas was moved through the pipe at a predetermined flow velocity of V. Note that in Experimental Example 1, the measured gas was moved from the left to the right of FIGS. 2 and 3. The same applied to Experimental Examples 2 to 22. At that time, a variation of the output of the sensor element with time and a variation of the power input to the heater with time were measured. It was assumed that the air inside the inner protection cover was completely replaced with the measured gas when the output of the sensor element was maximized. The ratio of the output of the sensor element to the highest value was obtained as a gas replacement ratio for the inside of the inner protection cover. Thus, the variation of the gas replacement ratio with time was obtained. The predetermined flow velocity V of the measured gas was set to 45 m/s, and the variation of the gas replacement ratio with time was obtained. Thereafter, the highest value of the power input to the heater of the sensor element 110 during a period of time from when the measured gas started to be moved to when the gas replacement ratio exceeds 90% was measured as the heater power (W). Note that if the flow velocity rapidly changes, the sensor element 110 is cooled and, thus, the heater power increases. Accordingly, if the measured value is low, the sensor element 110 does not easily get cold, that is, the heat keeping effect is high. In addition, the elapsed time from when the gas replacement ratio exceeds 10% to when the gas replacement ratio exceeds 90% after the measured gas is started to flow is defined as a response time (s) of gas concentration detection. The responsiveness of gas concentration detection increases with decreasing response time. Note that the measurement of the heater power and the response time was conducted a plurality of times for each of Experimental Examples, and the average of the values of the heater power and the average of the response time were defined as the heater power and the response time of Experimental Example.

Figure 25:
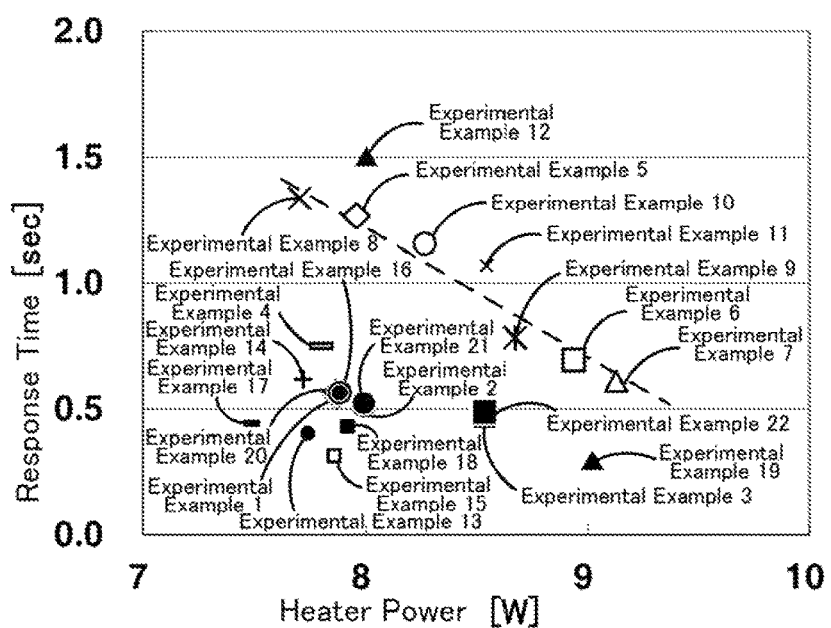
FIG. 25 is a graph indicating the heater power and the response time of each of Experimental Examples 1 to 22.

The values regarding the holes of each of the outer protection cover and the inner protection cover, the values regarding the gas flow channels, the distance A1, the distance A2, the distance A4, the distance A6, the distance B, the distance L, and the result of Evaluation Test 1 for each of Experimental Examples 1 to 22 are all shown in Table 1. Note that the heater power and the response time in Table 1 are the above-described averages, and the number of measurements for the heater power and the response time are also shown in Table 1. A graph that plots the heater power (the average value) and the response time (the average value) of each of Experimental Examples 1 to 22, which is the result of Evaluation Test 1, is shown in FIG. 25.

TABLE 1

| Cover | Outer Protection Cover | | | Inner Protection Cover | | | Distance A1 (mm) | Distance A2 (mm) | Distance A4 (mm) | Distance A6 (mm) | Distance B (mm) | Distance L (mm) | Heat Retaining | | Responsiveness | |
|---|---|---|---|---|---|---|---|---|---|---|---|---|---|---|---|---|
| | First Outer Gas Hole | Second Outer Gas Hole | Gas Flow Channel | Inner Gas Hole | | | | | | | | | Heater Power (W) | Number of Measurement | Response Time (s) | Number of Measurement |
| Experimental Example 1 | Diameter of 1 mm × 6 (Vertical Hole) | Diameter of 1 mm × 3 (Horizontal Hole) | Cylindrical Shape | Vertical Hole (Diameter of 1.5 mm × 1) | | | 0.6 | 1.9 | 0.5 | 1.6 | 2.7 | 4.0 | 7.87 | 3 | 0.55 | 3 |
| Experimental Example 2 | Diameter of 1 mm × 12 (Vertical Hole) | Diameter of 1 mm × 6 (Vertical Hole) | Cylindrical Shape | Vertical Hole (Diameter of 1.5 mm × 1) | | | 0.5 | 1.9 | 0.5 | 1.6 | 1.6 | 4.0 | 7.99 | 3 | 0.51 | 3 |
| Experimental Example 3 | Diameter of 1 mm × 12 (Vertical Hole) | Diameter of 1 mm × 6 (Vertical Hole) | Vertical Hole (4) | Vertical Hole (Diameter of 1.5 mm × 1) | | | 0.5 | 1.3 | — | 1.0 | 1.6 | 4.0 | 8.54 | 5 | 0.47 | 5 |
| Experimental Example 4 | Diameter of 1 mm × 6 (Vertical Hole) | Diameter of 1 mm × 3 (Horizontal Hole) | Horizontal Hole (6) with Regulation Member | Vertical Hole (Diameter of 1.5 mm × 1) | | | 0.5 | 1.8 | — | 1.6 | 2.7 | — | 7.80 | 4 | 0.75 | 4 |
| Experimental Example 5 | Diameter of 1 mm × 6 (Horizontal Hole) | Diameter of 1 mm × 6 (Horizontal Hole) | Horizontal Hole (6) with Regulation Member | Vertical Hole (Diameter of 1 mm × 1) | | | 6.0 | 1.8 | — | 1.6 | 2.7 | — | 7.96 | 9 | 1.27 | 41 |
| Experimental Example 6 | Diameter of 1 mm × 6 (Vertical Hole) | Diameter of 1.2 mm × 6 (Corner Hole) | Horizontal Hole (6) with Regulation Member | Horizontal Hole (Diameter of 1 mm × 4) | | | 6.2 | 3.6 | — | 1.6 | 2.7 | — | 8.84 | 6 | 0.70 | 4 |
| Experimental Example 7 | Diameter of 1 mm × 6 (Vertical Hole) | Diameter of 1 mm × 6 (Vertical Hole) | Horizontal Hole (6) with Regulation Member | Vertical Hole (Diameter of 1 mm × 1) | | | 8.0 | 1.8 | — | 1.6 | 2.7 | — | 9.13 | 6 | 0.61 | 4 |
| Experimental Example 8 | Diameter of 1 mm × 6 (Vertical Hole) | Diameter of 1 mm × 3 (Horizontal Hole) | Horizontal Hole (6) with Regulation Member | Vertical Hole (Diameter of 1 mm × 1) | | | 6.0 | 1.8 | — | 1.6 | 2.7 | — | 7.70 | 8 | 1.34 | 4 |
| Experimental Example 9 | Diameter of 1 mm × 6 (Vertical Hole) | Diameter of 1 mm × 3 (Vertical Hole) | Horizontal Hole (6) with Regulation Member | Horizontal Hole (Diameter of 1 mm × 4) | | | 6.2 | 3.6 | — | 1.6 | 2.7 | — | 8.67 | 5 | 0.78 | 4 |
| Experimental Example 10 | Diameter of 1 mm × 6 (Vertical Hole) | Diameter of 1 mm × 3 (Vertical Hole) | Horizontal Hole (6) with Regulation Member | Vertical Hole (Diameter of 1 mm × 1) | | | 6.0 | 1.8 | — | 1.6 | 2.7 | — | 8.27 | 6 | 1.16 | 4 |
| Experimental Example 11 | Diameter of 1 mm × 6 (Vertical Hole) | Diameter of 1 mm × 3 (Vertical Hole) | Horizontal Hole (6) with Regulation Member | Horizontal Hole (Diameter of 1 mm × 4) | | | 6.2 | 1.8 | — | 1.6 | 2.7 | — | 8.39 | 8 | 1.08 | 6 |
| Experimental Example 12 | Diameter of 1 mm × 6 (Vertical Hole) | Diameter of 1 mm × 3 (Vertical Hole) | Horizontal Hole (6) with Regulation Member | Horizontal Hole (Diameter of 1 mm × 4) | | | 6.2 | 2.5 | — | 2.5 | 2.7 | — | 8.01 | 6 | 1.49 | 6 |
| Experimental Example 13 | Diameter of 1 mm × 6 (Vertical Hole) | Diameter of 1 mm × 3 (Vertical Hole) | Cylindrical Shape | Vertical Hole (Diameter of 1.5 mm × 1) | | | 0.5 | 1.9 | 1.0 | 1.6 | 2.7 | 4.3 | 7.74 | 12 | 0.40 | 27 |
| Experimental Example 14 | Diameter of 1 mm × 6 (Vertical Hole) | Diameter of 1 mm × 3 (Vertical Hole) | Cylindrical Shape | Vertical Hole (Diameter of 1.5 mm × 1) | | | 0.5 | 2.4 | 0.5 | 2.1 | 2.7 | 4.3 | 7.72 | 3 | 0.62 | 3 |

TABLE 1-continued

| Cover | Outer Protection Cover | | Inner Protection Cover | | Distance A1 (mm) | Distance A2 (mm) | Distance A4 (mm) | Distance A6 (mm) | Distance B (mm) | Distance L (mm) | Heat Retaining | | Responsiveness | |
|---|---|---|---|---|---|---|---|---|---|---|---|---|---|---|
| | First Outer Gas Hole | Second Outer Gas Hole | Gas Flow Channel | Inner Gas Hole | | | | | | | Heater Power (W) | Number of Measurement | Response Time (s) | Number of Measurement |
| Experimental Example 15 | Diameter of 1 mm × 6 (Vertical Hole) | Diameter of 1 mm × 3 (Horizontal Hole) | Cylindrical Shape | Vertical Hole (Diameter of 1.5 mm × 1) | 1.0 | 1.8 | 1.0 | 1.6 | 2.7 | 4.3 | 7.86 | 3 | 0.31 | 3 |
| Experimental Example 16 | Diameter of 1 mm × 6 (Vertical Hole) | Diameter of 1 mm × 3 (Horizontal Hole) | Cylindrical Shape | Vertical Hole (Diameter of 1.5 mm × 1) | −0.6 | 1.9 | 1.0 | 1.6 | 2.7 | 4.3 | 7.38 | 3 | 0.56 | 3 |
| Experimental Example 17 | Diameter of 1 mm × 6 (Vertical Hole) | Diameter of 1 mm × 3 (Horizontal Hole) | Cylindrical Shape | Vertical Hole (Diameter of 1.5 mm × 1) | 0.5 | 1.9 | 1.0 | 1.6 | 2.7 | 5.3 | 7.47 | 3 | 0.44 | 3 |
| Experimental Example 18 | Diameter of 1 mm × 6 (Vertical Hole) | Diameter of 1 mm × 3 (Horizontal Hole) | Cylindrical Shape | Vertical Hole (Diameter of 1.5 mm × 1) | 0.5 | 1.9 | 1.0 | 1.6 | 2.7 | 3.3 | 7.92 | 3 | 0.43 | 3 |
| Experimental Example 19 | Diameter of 1.2 mm × 12 (Vertical Hole) | Diameter of 1.2 mm × 6 (Horizontal Hole) | Cylindrical Shape | Vertical Hole (Diameter of 1.5 mm × 1) | 0.5 | 1.9 | 0.5 | 1.6 | 0.6 | 4.3 | 9.02 | 3 | 0.28 | 3 |
| Experimental Example 20 | Diameter of 1 mm × 6 (Vertical Hole) | Diameter of 1 mm × 3 (Horizontal Hole) | Cylindrical Shape | Vertical Hole (Diameter of 1.5 mm × 1) | 0.6 | 1.9 | 0.5 | 1.6 | 2.7 | 4.3 | 7.87 | 3 | 0.56 | 3 |
| Experimental Example 21 | Diameter of 1 mm × 12 (Vertical Hole) | Diameter of 1 mm × 6 (Vertical Hole) | Cylindrical Shape | Vertical Hole (Diameter of 1.5 mm × 1) | 0.5 | 1.9 | 0.5 | 1.6 | 0.6 | 4.3 | 7.99 | 3 | 0.52 | 3 |
| Experimental Example 22 | Diameter of 1 mm × 12 (Vertical Hole) | Diameter of 1 mm × 6 (Vertical Hole) | Vertical Hole (4) | Vertical Hole (Diameter of 1.5 mm × 1) | 0.5 | 1.3 | — | 1.0 | 0.6 | 4.3 | 8.54 | 5 | 0.48 | 5 |

As can be clearly seen from Table 1 and FIG. 25, in Experimental Examples 5 to 12 that do not include the gas flow channel extending from the rear end side to the tip end side of the sensor element 110 and being open to the sensor element chamber 124 having the gas inlet port 111 disposed thereon and that do not have a distance A1 which is −5 mm or greater and 1.5 mm or less, a relationship between the heater power and the response time is located in the vicinity of the dashed line in FIG. 25, which indicates that there is a tradeoff between the heater power and the response time. In contrast, in Experimental Examples 1 to 3 and Experimental Examples 13 to 22 that include the gas flow channel extending from the rear end side to the tip end side of the sensor element 110 and being open to the sensor element chamber 124 having the gas inlet port 111 disposed thereon and Experimental Example 4 that has a distance A1 which is −5 mm or greater and 1.5 mm or less, the heater power is offset from the dashed line of FIG. 25 and is small and, in addition, the response time is small. That is, the tradeoff relationship does not exist and, thus, the responsiveness of gas concentration detection and the heat retaining properties can be maintained at the same time.

In addition, comparison of Experimental Example 11 and Experimental Example 12 that have the same configuration except for the distance A2 indicates that Experimental Example 12 having a longer distance A2 exhibits smaller heater power and a higher heat retaining property than Experimental Example 11. However, Experimental Example 12 exhibits a longer response time. In contrast, comparison of Experimental Example 2 and Experimental Example 3 indicates that Experimental Example 2 having a longer distance A2 exhibits smaller heater power and a higher heat retaining property than Experimental Example 3. The response time of Experimental Example 2 is not so long. This result indicates that the configuration that includes the gas flow channel extending from the rear end side to the tip end side of the sensor element and being open to the sensor element chamber having the gas inlet port 111 disposed thereon can more effectively prevent degradation of responsiveness (a longer response time). Note that when the similar experiment was conducted by changing only the distance A2 of Experimental Example 2 to a small value, substantially the same result as for Experimental Example 3 was obtained, although some configuration of the gas sensor of Experimental Example 2 differs from that of Experimental Example 3 in addition to the distance A2. This result indicates that a gas sensor of the configuration that has a gas flow channel extending from the rear end side to the tip end side of the sensor element and being open to the sensor element chamber having the gas inlet port 111 disposed thereon can increase the heat retaining property without significantly decreasing the responsiveness by increasing the distance A2 (i.e., by disposing the element-side opening of the gas flow channel away from the sensor element). In addition, the same applies to the distance A6. That is, comparison of Experimental Example 11 and Experimental Example 12 having the same configuration except for the distance A6 indicates that the heater power of Experimental Example 12 having a longer distance A6 is lower and, thus, the heat retaining property is higher, but the response time is longer. In contrast, comparison of Experimental Example 2 and Experimental Example 3 indicates that the heater power of Experimental Example 2 having a longer distance A6 is lower and, thus, the heat retaining property is higher, and the response time is not so longer.

[Evaluation Test 2]

A variation of the response time of each of Experimental Examples 1, 2, 5, 6, 13, 19, 20, and 21 was evaluated when soot in exhaust gas was deposited for a predetermined period of time. More specifically, the evaluation test was conducted as follows.

That is, each of the gas sensors of Experimental Examples 1, 2, 5, 6, 13, 19, 20, and 21 was attached to a pipe (having a diameter of 56 mm) in the same manner as in FIG. 1A and FIG. 1B. Thereafter, the pipe was connected to a 2.0L diesel engine, and exhaust gas serving as the measured gas was passed through the pipe for a predetermined period of time. The elapsed time is referred to as a "deposition time". Note that the diesel engine was operated under the following conditions: the rotational speed was 2000 rpm, the torque was 100 N, and the temperature of the exhaust gas was 200° C. In addition, the direction of the flow of the exhaust gas was set so as to be the same as the measured gas in Evaluation Test 1. After 24 hours of the deposition time elapsed, the diesel engine was stopped, and the response time (s) of the gas sensor was measured in the same manner as in Evaluation Test 1. The response time was considered as the response time when the deposition time was 24 hours. In the same manner, the response time when the deposition time was 48 hours was measured. Note that the measurement of the response time was conducted twice for each of Experimental Examples for each of the deposition times. The average of the values obtained through the two measurements was defined as the response time for each of Experimental Examples for each of the deposition times.

Figure 26:
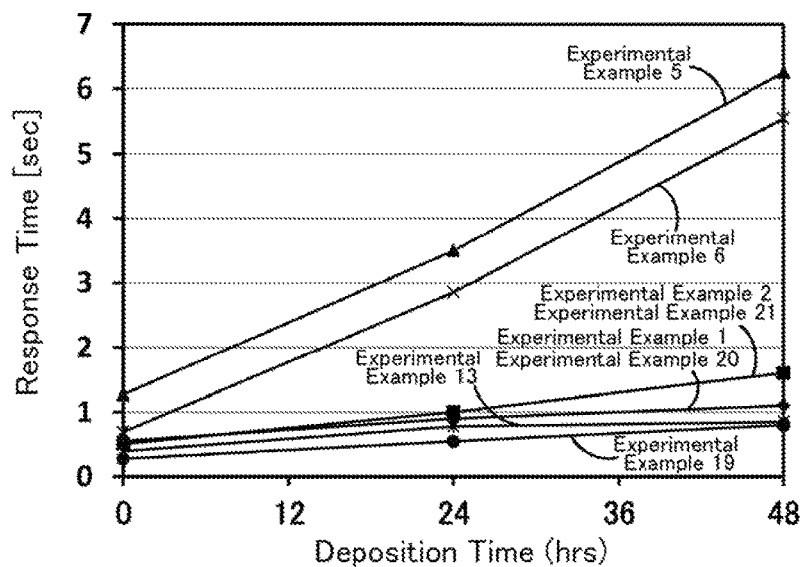
FIG. 26 is a graph indicating the deposition time and the response time of each of Experimental Examples 1, 2, 5, 6, 13, 19, 20, and 21.

Table 2 shows the result of Evaluation Test 2. In addition, FIG. 26 illustrates a graph in which the deposition time and the response time of each of Experimental Examples 1, 2, 5, 6, 13, 19, 20, and 21, which are the results of Evaluation Test 2, are plotted. Note that in Table 2 and FIG. 26, the response time measured in Evaluation Test 1 is shown as the response time when the deposition time is 0 hour.

| | Outer Protection Cover | | Inner Protection Cover | | | | | | | | Response Time(s) | | |
|---|---|---|---|---|---|---|---|---|---|---|---|---|---|
| Cover | First Outer Gas Hole | Second Outer Gas Hole | Gas Flow Channel | Inner Gas Hole | Distance A1 (mm) | Distance A2 (mm) | Distance A4 (mm) | Distance A6 (mm) | Distance B (mm) | Distance L (mm) | Deposition Time 0 (hr) | Deposition Time 24 (hr) | Deposition Time 48 (hr) |
| Experimental Example 1 | Diameter of 1 mm × 6 (Vertical Hole) Diameter of 1 mm × 6 (Horizontal Hole) | Diameter of 1 mm × 3 (Vertical Hole) Diameter of 1 mm × 3 (Horizontal Hole) | Cylindrical Shape | Vertical Hole (Diameter of 1.5 mm × 1) | 0.5 | 1.9 | 0.5 | 1.6 | 2.7 | 4.0 | 0.55 | 0.90 | 1.10 |

-continued

| | Outer Protection Cover | | Inner Protection Cover | | Distance A1 (mm) | Distance A2 (mm) | Distance A4 (mm) | Distance A6 (mm) | Distance B (mm) | Distance L (mm) | Reposnse Time(s) | | |
| | | | | | | | | | | | Deposition Time 0 (hr) | Deposition Time 24 (hr) | Deposition Time 48 (hr) |
| Cover | First Outer Gas Hole | Second Outer Gas Hole | Gas Flow Channel | Inner Gas Hole | | | | | | | | | |
|---|---|---|---|---|---|---|---|---|---|---|---|---|---|
| Experimental Example 2 | Diameter of 1 mm × 12 (Vertical Hole) | Diameter of 1 mm × 6 (Vertical Hole) | Cylindrical Shape | Vertical Hole (Diameter of 1.5 mm × 1) | 0.5 | 1.9 | 0.5 | 1.6 | 0.6 | 4.0 | 0.51 | 1.00 | 1.60 |
| Experimental Example 5 | Diameter of 1 mm × 6 (Horizontal Hole) | Diameter of 1 mm × 6 (Horizontal Hole) | Horizontal Hole (6) with Regulation Member | Vertical Hole (Diameter of 1 mm × 1) | 6.0 | 1.8 | — | 1.8 | 2.7 | — | 1.27 | 3.50 | 0.25 |
| Experimental Example 6 | Diameter of 1 mm × 6 (Corner Hole) | Diameter of 1.2 mm × 6 (Corner Hole) | Horizontal Hole (6) with Regulation Member | Horizontal Hole (Diameter of 1 mm × 4) | 6.2 | 3.6 | — | 1.8 | 2.7 | — | 0.70 | 2.65 | 5.55 |
| Experimental Example 13 | Diameter of 1 mm × 6 (Vertical Hole) Diameter of 1 mm × 6 (Horizontal Hole) | Diameter of 1 mm × 3 (Vertical Hole) Diameter of 1 mm × 3 (Horizontal Hole) | Cylindrical Shape | Vertical Hole (Diameter of 1.5 mm × 1) | 0.5 | 1.9 | 1.0 | 1.6 | 2.7 | 4.3 | 0.40 | 0.78 | 0.85 |
| Experimental Example 19 | Diameter of 1.2 mm × 12 (Vertical Hole) | Diameter of 1.2 mm × 6 (Vertical Hole) | Cylindrical Shape | Vertical Hole (Diameter of 1.5 mm × 1) | 0.5 | 1.9 | 0.5 | 1.6 | 0.6 | 4.3 | 0.28 | 0.55 | 0.80 |
| Experimental Example 20 | Diameter of 1 mm × 6 (Vertical Hole) Diameter of 1 mm × 6 (Horizontal Hole) | Diameter of 1 mm × 3 (Vertical Hole) Diameter of 1 mm × 3 (Horizontal Hole) | Cylindrical Shape | Vertical Hole (Diameter of 1.5 mm × 1) | 0.5 | 1.9 | 0.5 | 1.6 | 2.7 | 4.3 | 0.56 | 0.92 | 1.14 |
| Experimental Example 21 | Diameter of 1 mm × 12 (Vertical Hole) | Diameter of 1 mm × 6 (Vertical Hole) | Cylindrical Shape | Vertical Hole (Diameter of 1.5 mm × 1) | 0.5 | 1.9 | 0.5 | 1.6 | 0.6 | 4.3 | 0.52 | 1.03 | 1.64 |

As can be clearly seen from Table 2 and FIG. 26, unlike Experimental Examples 5 and 6, in Experimental Examples 1, 2, 13, 19, 20, and 21, the response time negligibly changes even when the deposition time is getting longer. That is, in Experimental Examples 1, 2, 13, 19, 20, and 21, even when the deposition time is getting longer, the response time negligibly becomes long. In Evaluation Test 2 for Experimental Example 5, the gas flow channel 227 formed in the cylinder portion 234 of the inner protection cover 230 (refer to FIG. 22) is clogged by deposited soot. Similarly, in Experimental Example 6, the gas flow channel 627 (refer to FIG. 23) is clogged by deposited soot. The deposition of soot clogs the gas flow channels 227 and 627 and, thus, the response time of each of Experimental Examples 5 and 6 is getting longer with increasing deposition time. In contrast, in Experimental Examples 1, 2, 13, 19, 20, and 21, although some soot is deposited in the outside opening 128 of the gas flow channel 127 (refer to FIG. 3), the gas flow channel 127 is only slightly clogged, as compared with Experimental Examples 5 and 6. Accordingly, even when the deposition time is getting longer, a variation in the response time is relatively prevented.

Note that Experimental Examples 1 to 4 and 13 to 22 correspond to examples of the present invention, and Experimental Examples 5 to 12 correspond to comparative examples. It should be noted that the present invention is not limited to the above-described example.

The present application claims priority from Japanese Patent Application No. 2013-116326 filed on May 31, 2013, the entire contents of which are incorporated herein by reference.

What is claimed is:

1. A gas sensor including:
   a sensor element having a tip end, a rear end opposite the tip end, a gas inlet port that allows measured gas to flow thereinto and capable of detecting concentration of predetermined gas in the measured gas that has flowed into the inside through the gas inlet port,
   an outer protection cover having an outer gas hole formed therein, where the outer gas hole allows the measured gas to flow from the outside to the inside therethrough, and covering the tip end of the sensor element, and
   a gas flow channel forming member disposed between the outer protection cover and the sensor element, where the gas flow channel forming member forms a gas flow channel which extends from the rear end side to the tip end side of the sensor element and is open to a space having the gas inlet port disposed therein in the pathway of the measured gas from the outer gas hole until the gas inlet port of the sensor element.

2. The gas sensor according to claim 1,
   wherein an element-side opening which is an opening of the gas flow channel adjacent to the space having the gas inlet port disposed therein is positioned at a distance A1 from the gas inlet port, the distance being measured in a direction extending from the rear end side to the tip end side of the sensor element, and a direction from the tip end side toward the rear end side is defined to be positive, and the distance A1 is greater than or equal to −5 mm and less than or equal to 1.5 mm.

3. The gas sensor according to claim 1,
wherein the gas flow channel forming member includes a first member and a second member, and the gas flow channel is a gap between the first member and the second member.

4. The gas sensor according to claim 3,
wherein the first member includes a first cylinder portion that surrounds the sensor element,
the second member includes a second cylinder portion having a diameter that is larger than that of the first cylinder portion, and
the gas flow channel is a cylindrical gap between the outer peripheral surface of the first cylinder portion and the inner peripheral surface of the second cylinder portion.

5. The gas sensor according to claim 4,
wherein at least one of the outer peripheral surface of the first cylinder portion and the inner peripheral surface of the second cylinder portion have a plurality of protruding portions formed thereon that protrude to the other one of the outer peripheral surface of the first cylinder portion and the inner peripheral surface of the second cylinder portion and that is in contact with the other surface.

6. The gas sensor according to claim 3,
wherein the first member includes a first cylinder portion that surrounds the sensor element,
the second member includes a second cylinder portion having a diameter that is larger than that of the first cylinder portion,
the outer peripheral surface of the first cylinder portion is in contact with the inner peripheral surface of the second cylinder portion and at least one of the outer peripheral surface of the first cylinder portion and the inner peripheral surface of the second cylinder portion have a concave portion formed thereon, and
the gas flow channel is a gap formed by the concave portion.

7. The gas sensor according to claim 1,
wherein the gas flow channel is a hole that passes through the gas flow channel forming member.

8. The gas sensor according to claim 1,
wherein the gas flow channel is formed in the pathway of the measured gas from the outer gas hole until the gas inlet port of the sensor element, and is a flow channel that extends from the rear end side to the tip end side of the sensor element and that is parallel to the rear-end to tip-end direction of the sensor element.

9. The gas sensor according to claim 1,
wherein the gas flow channel is formed in the pathway of the measured gas from the outer gas hole until the gas inlet port of the sensor element, and is a flow channel that extends from the rear end side to the tip end side of the sensor element and is inclined from the rear-end to tip-end direction so as to be closer to the sensor element toward the tip end of the sensor element from the rear end.

10. The gas sensor according to claim 1,
wherein the opening area of an element-side opening which is an opening of the gas flow channel adjacent to the space having the gas inlet port disposed therein is smaller than the opening area of an outside opening which is an opening on the space side where the space has the outer gas hole disposed therein.

11. The gas sensor according to claim 1,
wherein the sensor element is disposed at a position other than an area that is on an imaginary extension of the gas flow channel from an element-side opening which is an opening of the gas flow channel adjacent to the space having the gas inlet port disposed therein.

12. The gas sensor according to claim 1,
wherein an element-side opening which is an opening of the gas flow channel adjacent to the space having the gas inlet port disposed therein is open in a direction from the rear end to the tip end of the sensor element and is open parallel to the rear-end to tip-end direction of the sensor element.

13. The gas sensor according to claim 1, including a bottomed cylindrical inner protection cover disposed between the outer protection cover and the sensor element, where the bottomed cylindrical inner protection cover covers the tip end of the sensor element,
wherein the gas flow channel forming member constitutes at least part of the bottomed cylindrical inner protection cover.

14. The gas sensor according to claim 13,
wherein the inner protection cover has an inner gas hole formed therein, and the inner gas hole is located further away from the rear end than the gas flow channel in a direction toward the tip end of the sensor element.

15. The gas sensor according to claim 14,
wherein the outer protection cover includes a cylindrical body portion having a first outer gas hole representing the outer gas hole formed therein and a bottomed cylindrical tip end portion having a second outer gas hole formed therein, where the second outer gas hole is located away from the first outer gas hole in a direction toward the tip end of the sensor element, and having an internal diameter that is smaller than that of the cylindrical body portion,
a first gas chamber that communicates with the inside of the inner protection cover using the gas flow channel is formed between the cylindrical body portion of the outer protection cover and the inner protection cover, and
a second gas chamber that does not directly communicate with the first gas chamber and that communicates with the inside of the inner protection cover using the inner gas hole is formed between the tip end portion of the outer protection cover and the inner protection cover.

16. A gas sensor including:
a sensor element having a gas inlet port that allows measured gas to flow thereinto and capable of detecting concentration of predetermined gas in the measured gas that has flowed into the inside through the gas inlet port,
an outer protection cover having an outer gas hole formed therein, where the outer gas hole allows the measured gas to flow from the outside to the inside therethrough, and covering a tip end of the sensor element, and
a gas flow channel forming member disposed between the outer protection cover and the sensor element, where the gas flow channel forming member forms a gas flow channel which is open to a space having the gas inlet port disposed therein in the pathway of the measured gas from the outer gas hole until the gas inlet port of the sensor element,
wherein an element-side opening which is an opening of the gas flow channel adjacent to the space having the gas inlet port disposed therein is positioned at a distance A1 from the gas inlet port, the distance being measured in a direction extending from the rear end side to the tip end side of the sensor element, and a direction from the tip end side toward the rear end side is defined to be positive, and the distance A1 is greater than or equal to −5 mm and less than or equal to 1.5 mm.

17. The gas sensor according to claim 16,
wherein the gas flow channel forming member includes a first member and a second member, and the gas flow channel is a gap between the first member and the second member.

18. The gas sensor according to claim 17,
wherein the first member includes a first cylinder portion that surrounds the sensor element,
the second member includes a second cylinder portion having a diameter that is larger than that of the first cylinder portion,
the gas flow channel is a cylindrical gap between the outer peripheral surface of the first cylinder portion and the inner peripheral surface of the second cylinder portion, and
at least one of the outer peripheral surface of the first cylinder portion and the inner peripheral surface of the second cylinder portion have a plurality of protruding portions formed thereon that protrude to the other one of the outer peripheral surface of the first cylinder portion and the inner peripheral surface of the second cylinder portion and that is in contact with the other surface.

19. The gas sensor according to claim 17,
wherein the first member includes a first cylinder portion that surrounds the sensor element,
the second member includes a second cylinder portion having a diameter that is larger than that of the first cylinder portion,
the outer peripheral surface of the first cylinder portion is in contact with the inner peripheral surface of the second cylinder portion and at least one of the outer peripheral surface of the first cylinder portion and the inner peripheral surface of the second cylinder portion have a concave portion formed thereon, and
the gas flow channel is a gap formed by the concave portion.

20. The gas sensor according to claim 16,
wherein an element-side opening which is an opening of the gas flow channel adjacent to the space having the gas inlet port disposed therein is open in a direction from the rear end to the tip end of the sensor element and is open parallel to the rear-end to tip-end direction of the sensor element.

* * * * *